United States Patent
Gonzalez et al.

(10) Patent No.: US 10,443,065 B2
(45) Date of Patent: Oct. 15, 2019

(54) PLANT PROMOTOR AND 3' UTR FOR TRANSGENE EXPRESSION

(71) Applicant: Dow AgroSciences LLC, Indianapolis, IN (US)

(72) Inventors: Delkin O. Gonzalez, Zionsville, IN (US); Megan Sopko, Zionsville, IN (US); Jeffrey Church, Carmel, IN (US); James Patrick Connell, Indianapolis, IN (US); Kristina M. Woodall, Greenwood, IN (US); David Mann, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 208 days.

(21) Appl. No.: 15/233,328

(22) Filed: Aug. 10, 2016

(65) Prior Publication Data

US 2017/0051298 A1  Feb. 23, 2017

Related U.S. Application Data

(60) Provisional application No. 62/205,756, filed on Aug. 17, 2015.

(51) Int. Cl.
*C12N 15/00* (2006.01)
*C12N 15/63* (2006.01)
*C12N 15/82* (2006.01)

(52) U.S. Cl.
CPC ......... *C12N 15/8216* (2013.01); *C12N 15/00* (2013.01); *C12N 15/63* (2013.01)

(58) Field of Classification Search
None
See application file for complete search history.

(56) References Cited

U.S. PATENT DOCUMENTS

| 5,633,363 A | 5/1997 | Colbert et al. |
| 6,849,779 B1 | 2/2005 | Messing et al. |
| 2006/0141495 A1 * | 6/2006 | Wu ...................... C12Q 1/6895 435/6.11 |
| 2009/0119804 A1 | 5/2009 | Aukerman et al. |
| 2015/0067926 A1 | 3/2015 | Kumar et al. |

OTHER PUBLICATIONS

Wilson, R. GenEmbl Database, Acc. No. AC206176, "Maize Genome", Sep. 23, 2013.*
AC206176, Genbank Accession No. AC206176, *Zea mays* Cultivar B73 Chromosome 1 clone Ch201-46G-15 [Retrieved on Oct. 13, 2016]. Retrieved from the Internet <URL: https://www.ncbi.nlm.nih.gov/nuccore/AC206176>.
AC177830, Genbank Accession No. AC177830, *Zea mays* Cultivar B73 Chromosome 1 clone Ch201-40O19 [Retrieved on Oct. 13, 2016]. Retrieved from the Internet <URL: https://www.ncbi.nlm.nih.gov/nuccore/AC177830>.
Held, BM., et al., Zrp2: a novel maize gene whose mRNA accumulates in the root cortex and mature stems. Plant Molecular Biology. 1997. 35:367-375.
Le, T., et al. "Improving Nutritional Quality of Plant Proteins Through Genetic Engineering." Current genomics 17.3 (2016): 220-229.

* cited by examiner

*Primary Examiner* — Phuong T Bui

(57) ABSTRACT

This disclosure concerns compositions and methods for promoting transcription and translation of a nucleotide sequence in a plant or plant cell, employing a promoter and/or a 3'UTR from *Zea mays* Zrp2 gene. Some embodiments relate to a promoter from a *Zea mays* Zrp2 gene that is operably linked to a *Zea mays* Ubiquitin 1 intron and functions in plants to promote transcription of operably linked nucleotide sequences. Other embodiments relate to a 3' UTR from a *Zea mays* Zrp2 gene that functions in plants to terminate transcription of operably linked nucleotide sequences.

9 Claims, 3 Drawing Sheets

Specification includes a Sequence Listing.

Os Actin Promoter    aad1 gene    Zm Lipase 3'UTR

Truncated ZmZrp2 Promoter     phiYFP gene     ZmPer5

SEQUENCE LISTING

<160> NUMBER OF SEQ ID NOS: 9

<210> SEQ ID NO 1
<211> LENGTH: 1572
<212> TYPE: DNA
<213> ORGANISM: Zea mays

<400> SEQUENCE: 1

```
ggtagtgacg gttgtttggc aatagtaaaa tccagccctc tcccgtgggg aaaaaactgg      60
taggatctgg ctcgtggcta agattctctt tcttcccttt gtaaaaaaag agaagaaaaa     120
aaaaacgact gtcacggtgc cttgtctggt aatgatcgcg cggtcggctc tgtcctaacc     180
cgtaagatgg acgggagctg atgatagcgt gacctccaaa taaacaacaa gggcgtgttc     240
cccgcggtcg aatattttaa ggccactgga ttaggtgcgg ttgaatacat caacttcacg     300
aacatcatct gatctgatct gatttggtct gatatgatct gggtagtcat ttctgcaatg     360
agcatctatc aggtgaacca attaatattg atgacattat gagttcgaag atatactcta     420
aagtgttatc taaatacaga agacattcgt tcgttctttg cctataactc taaaaggctt     480
gtaacaccct cattcatcct ctatatacga agactctctc ctatcatttt tatcgattta     540
ttttttttat atttagacaa tggaattaaa tagaactaaa atatatataa gatgatatct     600
gaggacccga gatggtaatg gggactcgat cctcgattct ccacggagaa ttcctctagg     660
atataggtaa tttgtcccca cgaggattga aacggggtaa tttggtcccc atgtgcccgt     720
cccgcgaact tctcttgatc taaattagtc tatttccatg ttaaaactat actaaaaatt     780
taatacacag tctattataa aatagcaaac taaattctaa agttgatgca tcttgtaatt     840
ttaaatctgg tttgttcaag ttatattcat ttgatataat aaatttgaat ttgactctta     900
atatcgtatt ttttcctaac ggggacggat tctccacggg gataaattcc atgatacaga     960
tgggatgaaa gaaaaatctc ccgtatgaac ttttgcagga atggggatgg gccagagaaa    1020
ttttctccct gcggggacgg gggagccata tcctcggtgg agaatttccc attatcatcc    1080
ttatttgtgg tacatatata tgcataatct tttttttttg actgacatgt gggaaagtat    1140
cccatctcaa tagtagaaaa tcttgggaac ggtaggatcg aacacaaaga tcagctagct    1200
tgtaatcacc gagccatata gctagagggt aatagatcat gaatcaaatg ttttttttcat    1260
aaattattaa ggctctaaat tattttttaat ttaaaaataa ataaaaatat agttcgattc    1320
ttacatttta tagtgtaaaa ctttaaagtc tattattacc cctacttatt gagttatggt    1380
tcagttcttg tcgacggaga gtaatgagat atagaataag gtaccctata gaataaagaa    1440
tctttctctg aaaagtctga cgtacgtaaa taagatataa taaaaaaaat acaaagagaa    1500
gcgctggact ggagatgctc ctatatgcgg caatgcctgt gcttataaat agccacctcg    1560
gtcggcaagg ac                                                        1572
```

<210> SEQ ID NO 2
<211> LENGTH: 1057
<212> TYPE: DNA
<213> ORGANISM: zea mays

<400> SEQUENCE: 2

```
agatctcccc caaatccacc cgtcggcacc tccgcttcaa ggtacgccgc tcgtcctccc      60
cccccccccc cctctctacc ttctctagat cggcgttccg gtccatgcat ggttagggcc     120
cggtagttct acttctgttc atgtttgtgt tagatccgtg tttgtgttag atccgtgctg     180
ctagcgttcg tacacggatg cgacctgtac gtcagacacg ttctgattgc taacttgcca     240
```

```
gtgtttctct ttggggaatc ctgggatggc tctagccgtt ccgcagacgg gatcgatttc      300 atgattttt ttgtttcgtt gcatagggtt tggtttgccc ttttccttta tttcaatata      360
tgccgtgcac ttgtttgtcg ggtcatcttt tcatgctttt ttttgtcttg gttgtgatga     420
tgtggtctgg ttgggcggtc gttctagatc ggagtagaat tctgtttcaa actacctggt    480
ggatttatta attttggatc tgtatgtgtg tgccatacat attcatagtt acgaattgaa    540
gatgatggat ggaaatatcg atctaggata ggtatacatg ttgatgcggg ttttactgat   600
gcatatacag agatgctttt tgttcgcttg gttgtgatga tgtggtgtgg ttgggcggtc   660
gttcattcgt tctagatcgg agtagaatac tgtttcaaac tacctggtgt atttattaat  720
tttggaactg tatgtgtgtg tcatacatct tcatagttac gagtttaaga tggatggaaa  780
tatcgatcta ggataggtat acatgttgat gtgggtttta ctgatgcata tacatgatgg  840
catatgcagc atctattcat atgctctaac cttgagtacc tatctattat aataaacaag   900
tatgttttat aattatttcg atcttgatat acttggatga tggcatatgc agcagctata   960
tgtggatttt tttagccctg ccttcatacg ctatttattt gcttggtact gtttctttg   1020 tcgatgctca ccctgttgtt tggtgttact tctgcag                            1057

<210> SEQ ID NO 3
<211> LENGTH: 500
<212> TYPE: DNA
<213> ORGANISM: zea mays

<400> SEQUENCE: 3
agtgaagcct aatagcgtta agtacccgtg ctcagagctc tatctgtaac ctgtatggac   60
ctaatgtggc tctgtaatgc taaataaaac ctgcgtcaat catgtatcgt gatatttat  120 ttgttttagc aaaatggtgt ccaaaactat agtccaaagt gaaggaattc atgttgtgag 180
cactatattt ggcacctgaa catggttgga cggttcgacc aaatggcccg gacgatccgt  240
gcacgcgatc agattaactc ggtcatgagt acttattaca tgcatggcta tcctaaccta  300
tttatggtaa tctgtttaat ctcgcctaga aacaggtcca gatcttatct cctatacata  360
taaagggata cagctgattg agaaccttcg aacatatttc aatcgaacca atttatttac  420
cttcatttat cattcatgtc ttcggattag atgtatcgta gctttagttg tagattccac  480
ctagcaattt ctatctccat                                               500

<210> SEQ ID NO 4
<211> LENGTH: 4002
<212> TYPE: DNA
<213> ORGANISM: artificial sequence
<220> FEATURE:
<223> OTHER INFORMATION: Zea mays Zrp2 promoter (Zea mays Ubi1
      intron)::phi-YFP gene::Zea mays Zrp2 3'UTR

<400> SEQUENCE: 4
ggtagtgacg gttgtttggc aatagtaaaa tccagccctc tcccgtgggg aaaaaactgg    60
taggatctgg ctcgtggcta agattctctt tcttcccttt gtaaaaaaag agaagaaaaa   120
aaaaacgact gtcacggtgc cttgtctggt aatgatcgcg cggtcggctc tgtcctaacc  180
cgtaagatgg acgggagctg atgatagcgt gacctccaaa taaacaacaa gggcgtgttc 240
cccgcggtcg aatattttaa gggccactga ttaggtgcgg ttgaatacat caacttcacg 300
aacatcatct gatctgatct gatttggtct gatatgatct gggtagtcat ttctgcaatg 360
agcatctatc aggtgaacca attaatattg atgacattat gagttcgaag atatactcta 420
```

```
aagtgttatc taaatacaga agacattcgt tcgttctttg cctataactc taaaaggctt      480
gtaacaccct cattcatcct ctatatacga agactctctc ctatcatttt tatcgattta      540
ttttttttat atttagacaa tggaattaaa tagaactaaa atatatataa gatgatatct      600
gaggacccga gatggtaatg gggactcgat cctcgattct ccacggagaa ttcctctagg      660
atataggtaa tttgtcccca cgaggattga aacggggtaa tttggtcccc atgtgcccgt      720
cccgcgaact tctcttgatc taaattagtc tatttccatg ttaaaactat actaaaatt       780 taatacacag tctattataa aatagcaaac taaattctaa agttgatgca tcttgtaatt      840
ttaaatctgg tttgttcaag ttatattcat ttgatataat aaatttgaat ttgactctta      900
atatcgtatt ttttcctaac ggggacggat tctccacggg gataaattcc atgatacaga      960
tgggatgaaa gaaaaatctc ccgtatgaac ttttgcagga atggggatgg ccagagaaa      1020 ttttctccct gcggggacgg gggagccata tcctcggtgg agaatttccc attatcatcc     1080
ttatttgtgg tacatatata tgcataatct ttttttttg actgacatgt gggaaagtat      1140
cccatctcaa tagtagaaaa tcttgggaac ggtaggatcg aacacaaaga tcagctagct     1200
tgtaatcacc gagccatata gctagagggt aatagatcat gaatcaaatg ttttttttcat    1260 aaattattaa ggctctaaat tattttttaat ttaaaaataa ataaaaatat agttcgattc    1320
ttacatttta tagtgtaaaa ctttaaagtc tattattacc cctacttatt gagttatggt     1380
tcagttcttg tcgacggaga gtaatgagat atagaataag gtaccctata gaataaagaa    1440
tctttctctg aaaagtctga cgtacgtaaa taagatataa taaaaaaaat acaaagagaa     1500
gcgctggact ggagatgctc ctatatgcgg caatgcctgt gcttataaat agccacctcg     1560
gtcggcaagg acagatctcc cccaaatcca cccgtcggca cctccgcttc aaggtacgcc     1620
gctcgtcctc cccccccccc cccctctcta ccttctctag atcggcgttc cggtccatgc     1680
atggttaggg cccggtagtt ctacttctgt tcatgtttgt gttagatccg tgtttgtgtt     1740
agatccgtgc tgctagcgtt cgtacacgga tgcgacctgt acgtcagaca cgttctgatt     1800
gctaacttgc cagtgtttct ctttggggaa tcctgggatg gctctagccg ttccgcagac     1860
gggatcgatt tcatgatttt ttttgtttcg ttgcataggg tttggtttgc ccttttcctt     1920
tatttcaata tatgccgtgc acttgttttgt cgggtcatct tttcatgctt ttttttgtct    1980
tggttgtgat gatgtggtct ggttgggcgg tcgttctaga tcggagtaga attctgtttc     2040
aaactacctg gtggatttat taattttgga tctgtatgtg tgtgccatac atattcatag     2100
ttacgaattg aagatgatgg atggaaatat cgatctagga taggtataca tgttgatgcg     2160
ggttttactg atgcatatac agagatgctt tttgttcgct tggttgtgat gatgtggtgt     2220
ggttgggcgg tcgttcattc gttctagatc ggagtagaat actgtttcaa actacctggt     2280
gtatttatta attttggaac tgtatgtgtg tgtcatacat cttcatagtt acgagtttaa     2340
gatggatgga aatatcgatc taggataggt atacatgttg atgtgggttt tactgatgca     2400
tatacatgat ggcatatgca gcatctattc atatgctcta accttgagta cctatctatt     2460
ataataaaca agtatgtttt taattattt cgatcttgat atacttggat gatggcatat      2520
gcagcagcta tatgtggatt tttttagccc tgccttcata cgctatttat ttgcttggta     2580
ctgtttcttt tgtcgatgct caccctgttg tttggtgtta cttctgcagg tacagtagtt     2640
agttgaggta ccggatccac acgacaccat ggcatctgga gcacttctct ttcatgggaa     2700
gattccttac gttgtggaga tggaagggaa tgttgatggc cacaccttta gcatacgtgg    2760
```

-continued

```
gaaaggctac ggagatgcct cagtgggaaa ggttgatgca cagttcatct gcacaactgg    2820
tgatgttcct gtgccttgga gcacacttgt caccactctc acctatggag cacagtgctt    2880
tgccaagtat ggtccagagt tgaaggactt ctacaagtcc tgtatgccag atggctatgt    2940
gcaagagcgc acaatcacct tgaaggaga tggcaacttc aagactaggg ctgaagtcac     3000
ctttgagaat gggtctgtct acaatagggt caaactcaat ggtcaaggct tcaagaaaga    3060
tggtcatgtg ttgggaaaga acttggagtt caacttcact ccccactgcc tctacatctg    3120
gggtgaccaa gccaaccacg gtctcaagtc agccttcaag atctgtcatg agattactgg    3180
cagcaaaggc gacttcatag tggctgacca cacccagatg aacactccca ttggtggagg    3240
tccagttcat gttccagagt atcatcacat gtcttaccat gtgaaacttt ccaaagatgt    3300
gacagaccac agagacaaca tgtccttgaa agaaactgtc agagctgttg actgtcgcaa    3360
gacctacctt tgagtagtta gcttaatcac ctagagctct ctacgagcaa cacgtccact    3420
aggatcagca gctgtcagtg acagataaga taacggcgca attacctaat ctgcgtagta    3480
cgagcagcgg taacctttaa acagtgaagc ctaatagcgt taagtacccg tgctcagagc    3540
tctatctgta acctgtatgg acctaatgtg gctctgtaat gctaaataaa acctgcgtca    3600
atcatgtatc gtgatatttt atttgtttta gcaaaatggt gtccaaaact atagtccaaa    3660
gtgaaggaat tcatgttgtg agcactatat ttggcacctg aacatggttg acggttcga    3720 ccaaatggcc cggacgatcc gtgcacgcga tcagattaac tcggtcatga gtacttatta    3780
catgcatggc tatcctaacc tatttatggt aatctgttta atctcgccta gaaacaggtc    3840
cagatcttat ctcctataca tataaaggga tacagctgat tgagaacctt cgaacatatt    3900
tcaatcgaac caatttattt accttcattt atcattcatg tcttcggatt agatgtatcg    3960
tagctttagt tgtagattcc acctagcaat ttctatctcc at                       4002
```

<210> SEQ ID NO 5
<211> LENGTH: 2673
<212> TYPE: DNA
<213> ORGANISM: artificial sequence
<220> FEATURE:
<223> OTHER INFORMATION: Oryza sativa Actin promoter:: aad1 gene::Zea mays Lipase 3'UTR

<400> SEQUENCE: 5

```
ctcgaggtca ttcatatgct tgagaagaga gtcgggatag tccaaaataa aacaaaggta     60
agattacctg gtcaaaagtg aaaacatcag ttaaaggtg gtataaagta aaatatcggt     120
aataaaaggt ggcccaaagt gaaatttact cttttctact attataaaaa ttgaggatgt    180
ttttgtcggt actttgatac gtcattttg tatgaattgg ttttttaagtt tattcgcttt    240 tggaaatgca tatctgtatt tgagtcgggt tttaagttcc tttgcttttg taaatacaga    300
gggatttgta taagaaatat ctttaaaaaa acccatatgc taatttgaca taattttga    360 gaaaaatata tattcaggcg aattctcaca atgaacaata ataagattaa aatagctttc    420
ccccgttgca gcgcatgggt atttttcta gtaaaaataa aagataaact tagactcaaa    480
acatttacaa aaacaacccc taagttcct aaagcccaaa gtgctatcca cgatccatag    540
caagcccagc ccaacccaac ccaacccaac ccaccccagt ccagccaact ggacaatagt    600
ctccacaccc cccactatc accgtgagtt gtccgcacgc accgcacgtc tcgcagccaa    660
aaaaaaaaaa agaagaaaaa aaagaaaaa gaaaaacag caggtgggtc cgggtcgtgg    720
gggccggaaa cgcgaggagg atcgcgagcc agcgacgagg ccggccctcc ctccgcttcc    780
```

```
aaagaaacgc cccccatcgc cactatatac atacccccc ctctcctccc atcccccaa      840
ccctaccacc accaccacca ccacctccac ctcctccccc ctcgctgccg gacgacgcct    900
cccccctccc cctccgccgc cgccgcgccg gtaaccaccc cgcccctctc ctctttcttt    960
ctccgttttt tttttccgtc tcggtctcga tctttggcct tggtagtttg ggtgggcgag   1020
aggcggcttc gtgcgcgccc agatcggtgc gcgggagggg cgggatctcg cggctggggc   1080
tctcgccggc gtggatccgg cccggatctc gcggggaatg gggctctcgg atgtagatct   1140
gcgatccgcc gttgttgggg gagatgatgg ggggtttaaa atttccgcca tgctaaacaa   1200
gatcaggaag aggggaaaag ggcactatgg tttatatttt tatatatttc tgctgcttcg   1260
tcaggcttag atgtgctaga tctttctttc ttcttttgt gggtagaatt tgaatccctc    1320
agcattgttc atcggtagtt tttcttttca tgatttgtga caaatgcagc ctcgtgcgga   1380
gcttttttgt aggtagacca tggctcatgc tgccctcagc cctctctccc aacgctttga   1440
gagaatagct gtccagccac tcactggtgt ccttggtgct gagatcactg gagtggactt   1500
gagggaacca cttgatgaca gcacctggaa tgagatattg gatgccttcc acacttacca   1560
agtcatctac tttcctggcc aagcaatcac caatgagcag cacattgcat tctcaagaag   1620
gtttggacca gttgatccag tgcctcttct caagagcatt gaaggctatc agaggttca    1680
gatgatccgc agagaagcca atgagtctgg aagggtgatt ggtgatgact ggcacacaga   1740
ctccactttc cttgatgcac ctccagctgc tgttgtgatg agggccatag atgttcctga   1800
gcatggcgga gacactgggt tcctttcaat gtacacagct gggagacct  tgtctccaac   1860
catgcaagcc accatcgaag ggctcaacgt tgtgcactct gccacacgtg tgttcggttc   1920
cctctaccaa gcacagaacc gtcgcttcag caacacctca gtcaaggtga tggatgttga   1980
tgctggtgac agagagacag tccatcccct tggttgtgact catcctggct ctggaaggaa   2040
aggcctttat gtgaatcaag tctactgtca gagaattgag gcatgacag atgcagaatc    2100
aaagccattg cttcagttcc tctatgagca tgccaccaga tttgacttca cttgccgtgt   2160
gaggtggaag aaagaccaag tccttgtctg ggacaacttg tgcaccatgc accgtgctgt   2220
tcctgactat gctggcaagt tcagatactt gactcgcacc acagttggtg gagttaggcc   2280
tgcccgctga gtagttagct taatcaccta gagctcggtc gcagcgtgtg cgtgtccgtc   2340
gtacgttctg gccggccggg ccttgggcgc gcgatcagaa gcgttgcgtt ggcgtgtgtg   2400
tgcttctggt ttgctttaat tttaccaagt ttgtttcaag gtggatcgcg tggtcaaggc   2460
ccgtgtgctt taaagaccca ccggcactgg cagtgagtgt tgctgcttgt gtaggctttg   2520
gtacgtatgg gctttatttg cttctggatg ttgtgtacta cttgggtttg ttgaattatt   2580
atgagcagtt gcgtattgta attcagctgg gctacctgga cattgttatg tattaataaa   2640
tgctttgctt tcttctaaag atctttaagt gct                                 2673
```

<210> SEQ ID NO 6
<211> LENGTH: 2629
<212> TYPE: DNA
<213> ORGANISM: artificial sequence
<220> FEATURE:
<223> OTHER INFORMATION: Zea mays Zrp2 promoter operably linked to the
      Zea mays Ubi1 intron

<400> SEQUENCE: 6

```
ggtagtgacg gttgtttggc aatagtaaaa tccagccctc tcccgtgggg aaaaaactgg     60
taggatctgg ctcgtggcta agattctctt tcttcccttt gtaaaaaaag agaagaaaaa    120
```

```
aaaaacgact gtcacggtgc cttgtctggt aatgatcgcg cggtcggctc tgtcctaacc      180
cgtaagatgg acgggagctg atgatagcgt gacctccaaa taaacaacaa gggcgtgttc      240
cccgcggtcg aatattttaa gggccactga ttaggtgcgg ttgaatacat caacttcacg      300
aacatcatct gatctgatct gatttggtct gatatgatct gggtagtcat ttctgcaatg      360
agcatctatc aggtgaacca attaatattg atgacattat gagttcgaag atatactcta      420
aagtgttatc taaatacaga agacattcgt tcgttctttg cctataactc taaaaggctt      480
gtaacaccct cattcatcct ctatatacga agactctctc ctatcatttt tatcgattta      540
ttttttttat atttagacaa tggaattaaa tagaactaaa atatatataa gatgatatct      600
gaggacccga gatggtaatg gggactcgat cctcgattct ccacggagaa ttcctctagg      660 ataggtaa tttgtcccca cgaggattga acgggtaa tttggtcccc atgtgcccgt         720
cccgcgaact tctcttgatc taaattagtc tatttccatg ttaaaactat actaaaaatt      780
taatacacag tctattataa aatagcaaac taaattctaa agttgatgca tcttgtaatt      840
ttaaatctgg tttgttcaag ttatattcat ttgatataat aaatttgaat ttgactctta      900
atatcgtatt ttttcctaac ggggacggat tctccacggg gataaattcc atgatacaga      960
tgggatgaaa gaaaaatctc ccgtatgaac ttttgcagga atggggatgg gccagagaaa     1020
ttttctccct gcggggacgg gggagccata tcctcggtgg agaatttccc attatcatcc     1080
ttatttgtgg tacatatata tgcataatct ttttttttg actgacatgt gggaaagtat      1140
cccatctcaa tagtagaaaa tcttgggaac ggtaggatcg aacacaaaga tcagctagct     1200
tgtaatcacc gagccatata gctagagggt aatagatcat gaatcaaatg ttttttttcat    1260 aaattattaa ggctctaaat tatttttaat ttaaaaataa ataaaaatat agttcgattc     1320
ttacatttta tagtgtaaaa ctttaaagtc tattattacc cctacttatt gagttatggt     1380
tcagttcttg tcgacggaga gtaatgagat atagaataag gtaccctata gaataaagaa     1440
tctttctctg aaaagtctga cgtacgtaaa taagatataa taaaaaaaat acaaagagaa     1500
gcgctggact ggagatgctc ctatatgcgg caatgcctgt gcttataaat agccacctcg     1560
gtcggcaagg acagatctcc cccaaatcca cccgtcggca cctccgcttc aaggtacgcc     1620
gctcgtcctc ccccccccc cccctctcta ccttctctag atcggcgttc cggtccatgc      1680
atggttaggg cccggtagtt ctacttctgt tcatgtttgt gttagatccg tgttgtgtt      1740 agatccgtgc tgctagcgtt cgtacacgga tgcgacctgt acgtcagaca cgttctgatt     1800
gctaacttgc cagtgtttct ctttggggaa tcctgggatg gctctagccg ttccgcagac     1860
gggatcgatt tcatgatttt ttttgtttcg ttgcataggg tttggtttgc ccttttcctt     1920
tatttcaata tatgccgtgc acttgttgt cgggtcatct tttcatgctt ttttttgtct      1980
tggttgtgat gatgtggtct ggttgggcgg tcgttctaga tcggagtaga attctgtttc     2040
aaactacctg gtggatttat taattttgga tctgtatgtg tgtgccatac atattcatag     2100
ttacgaattg aagatgatgg atggaaatat cgatctagga taggtataca tgttgatgcg     2160
ggttttactg atgcatatac agagatgctt tttgttcgct tggttgtgat gatgtggtgt     2220
ggttgggcgg tcgttcattc gttctagatc ggagtagaat actgtttcaa actacctggt     2280
gtatttatta attttggaac tgtatgtgtg tgtcatacat cttcatagtt acgagtttaa     2340
gatggatgga aatatcgatc taggataggt atacatgttg atgtgggttt tactgatgca     2400
tatacatgat ggcatatgca gcatctattc atatgctcta accttgagta cctatctatt     2460
ataataaaca agtatgtttt ataattattt cgatcttgat atacttggat gatggcatat     2520
```

| | |
|---|---|
| gcagcagcta tatgtggatt tttttagccc tgccttcata cgctatttat ttgcttggta | 2580 |
| ctgtttcttt tgtcgatgct caccctgttg tttggtgtta cttctgcag | 2629 |

<210> SEQ ID NO 7
<211> LENGTH: 2082
<212> TYPE: DNA
<213> ORGANISM: Zea mays

<400> SEQUENCE: 7

| | |
|---|---|
| atgcatacaa gagcaacaag atactggcgc agaggagcaa tgcccggcat ggatgccttc | 60 |
| gctgctgtgt cactactcgc cacactcttt ctggttcgtg cggcagctgc ccatcctccg | 120 |
| gcggcggctg cggacgccat gacgccgacg gactattggc gagcggtgct tcctgagacc | 180 |
| ccgatgcccc gagccatact cgacctattg accacatcta cagttggtga gggctcaagg | 240 |
| aaggtcacca cgtcaaatgg gtaccaaggc catgacttaa gaacggtcag cacatcatat | 300 |
| gcatctcaag atggggacaa ctcatggaag gccaccatgt catatgggtt ccaaagtggt | 360 |
| gagggctcga ggaaggtcac cacatcatat ccgtaccgag ggcaggactt aaggatggtc | 420 |
| agcacatcat atgtatctca agatgaggac aactcatgga aggtctcaat gccatctagg | 480 |
| ttccaagttg gtgagggctc aaggaaggtc accacgtcaa atgggtacca aggccatgac | 540 |
| ttaaggacgg tcagcacatc atatgcatct caagatgggg acaactcatg gaaggccacc | 600 |
| atgtcatatg ggttccaaag tggtgagggc tcgaggaagg tcaccacatc atatccgtac | 660 |
| cgaggccagg acttaaggat ggtcagcaca tcatatgtat ctcaagatga ggacaactca | 720 |
| tggaaggtct caatgccatc taggttccaa gttggtgagg gctcaaggaa ggtcaccacg | 780 |
| tcaaatgggt accaaggcca tgacttaagg acggtcagca catcatatgc atctcaagat | 840 |
| ggggacaact catggaaggc caccatgtca tatgggttcc aaagtggtga gggctcgagg | 900 |
| aaggtcacca catcatatcc gtaccgaggc caggacttaa ggatggtcag cacatcatat | 960 |
| gtatctcaag atgaggacaa ctcatggaag gtctcgatgc catctaggtt ccaagttggt | 1020 |
| gagggctcaa ggaagctcac cacaccattc gaatcacaaa gggaggactc aaggaaggcc | 1080 |
| accgcatcat atggaatcca agatgatgag gacacaagga aggccactac atcatatgga | 1140 |
| atccatgggg aggacccaag aaaggccacc acgtcatatg gttcccagga tgagaaggga | 1200 |
| tcaaggaagg tcataatgtc atatgggtct aatggtgagg atgatccaag aaaggccacc | 1260 |
| acatcatatg gaatacaaga taaagagtat cccaggaagg ccaccacatc ttatggagtt | 1320 |
| caaggggaca tccatcacca tgaccatgct gccgttcaca tccacagcag cggcaacaag | 1380 |
| ctagtagcag atgttttctt cttccacgac gtcctacgcc agggtccgt aatcacgccg | 1440 |
| atcatcccac cgaccatcac cctaccacct ctgctgcctc ccgcgaggc cgacgcgctc | 1500 |
| ccgttctcca ccgggcgctt cgccgacatc ctcgccatgt cgcgccgac gacatccgac | 1560 |
| gccatgggcg aagagatacg gtcgacgctc gacacctgcg agaacacgcg cccgctccct | 1620 |
| ggcgagaagg ccgcctgcgc cacctccctc gagtctctcg ccaggatacc cgccgtcctc | 1680 |
| ctcgggacac gcaacgtccg cgctttctcc ggcgacatgc ccaccgatcc tgccggcacg | 1740 |
| tcggcgaagc gggggcggta acgtaacg gccgtgcaga agctctccga gtcactgacg | 1800 |
| gcggcggcgt gccatgacct gacgtacccc tacgttgtgt tctactgcca cacgaccaac | 1860 |
| ccagcggcca cgtacctggt gaagctggca gcccaggatg gcgggacgcc ggacatggag | 1920 |
| gcgttggtcg tgtgccacct cgacacgtcg ttgtggagtc ccagacaccc attcttggtg | 1980 |

```
gcgcacagtc tcaagccagg ggacgacgca gtcgtgtgcc attttctctc taagctcagc    2040
atcgtctggg tccccgctgg cgagcagggg tggcgtgcgt ga                       2082

<210> SEQ ID NO 8
<211> LENGTH: 1818
<212> TYPE: DNA
<213> ORGANISM: Zea mays

<400> SEQUENCE: 8
atgcatacaa gagcaacaag atactggcgc agaggagcaa tgcccggcat ggatgccttc      60
gctgctgtgt cactactcgc cacactcttt ctggttcgtg cggcagctgc ccatcctccg     120
gcggcggctg cggacgccat gacgccgacg gactattggc gagcggtgct tcctgagacc     180
ccgatgcccc gagccatact cgacctattg accacatcta cagttggtga gggctcaagg     240
aaggtcacca cgtcaaatgg gtaccaaggc catgacttaa ggacggtcag cacatcatat     300
gcatctcaag atggggacaa ctcatggaag gccaccatgt catatgggtt ccaaagtggt     360
gagggctcga ggaaggtcac cacatcatat ccgtaccgag gccaggactt aaggatggtc     420
agcacatcat atgtatctca agatgaggac aactcatgga aggtctcaat gccatctagg     480
ttccaagttg gtgagggctc aaggaaggtc accacgtcaa atgggtacca aggccatgac     540
ttaaggacgg tcagcacatc atatgcatct caagatgggg acaactcatg gaaggccacc     600
atgtcatatg ggttccaaag tggtgagggc tcgaggaagg tcaccacatc atatccgtac     660
cgaggccagg acttaaggat ggtcagcaca tcatatgtat ctcaagatga ggacaactca     720
tggaaggtct cgatgccatc taggttccaa gttggtgagg gctcaaggaa gctccaccaca     780 ccattcgaat cacaaaggga ggactcaagg aaggccaccg catcatatgg aatccaagat     840
gatgaggaca caaggaaggc cactacatca tatggaatcc atggggagga cccaagaaag     900
gccaccacgt catatggttc ccaggatgag aagggatcaa ggaaggtcat aatgtcatat     960
gggtctaatg gtgaggatga tccaagaaag gccaccacat catatggaat acaagataaa    1020
gagtatccca ggaaggccac cacatcttat ggagttcaag gggacatcca tcaccatgac    1080
catgctgccg ttcacatcca cagcagcggc aacaagctag tagcagatgt tttcttcttc    1140
cacgacgtcc tacgcccagg gtccgtaatc acgccgatca tcccaccgac catcacccta    1200
ccacctctgc tgcctctccg cgaggccgac gcgctcccgt tctccaccgg cgcttcgcc     1260 gacatcctcg ccatgttcgc gccgacgaca tccgacgcca tgggcgaaga gatacggtcg    1320 acgtcgaca cctgcgagaa cacgcgcccc ctccctggcg agaaggccgc ctgcgccacc     1380
tccctcgagt ctctcgccag gatacccgcc gtcctcctcg gacacgcaa cgtccgcgct     1440 ttctccggcg acatgcccac cgatcctgcc ggcacgtcgg cgaagcgggg gcggtataac    1500
gtaacggccg tgcagaagct ctccgagtca ctgacggcgg cggcgtgcca tgacctgacg    1560 taccctacg ttgtgttcta ctgccacacg accaacccag cggccacgta cctggtgaag    1620
ctggcagccc aggatggcgg gacgccggac atggaggcgt tggtcgtgtg ccacctcgac    1680
acgtcgttgt ggagtcccag acacccattc ttggtggcgc acagtctcaa gccaggggac    1740
gacgcagtcg tgtgccattt tctctctaag ctcagcatcg tctgggtccc cgctggcgag    1800
caggggtggc gtgcgtga                                                  1818

<210> SEQ ID NO 9
<211> LENGTH: 3867
<212> TYPE: DNA
<213> ORGANISM: artificial sequence
```

<220> FEATURE:
<223> OTHER INFORMATION: Zea mays Zrp2 promoter (Zea mays Ubi1 intron)::phi-YFP gene::Zea mays Per 5 3'UTR

<400> SEQUENCE: 9

```
ggtagtgacg gttgtttggc aatagtaaaa tccagccctc tcccgtgggg aaaaaactgg      60
taggatctgg ctcgtggcta agattctctt tcttcccttt gtaaaaaaag agaagaaaaa     120
aaaaacgact gtcacggtgc cttgtctggt aatgatcgcg cggtcggctc tgtcctaacc     180
cgtaagatgg acgggagctg atgatagcgt gacctccaaa taaacaacaa gggcgtgttc     240
cccgcggtcg aatattttaa gggccactga ttaggtgcgg ttgaatacat caacttcacg     300
aacatcatct gatctgatct gatttggtct gatatgatct gggtagtcat ttctgcaatg     360
agcatctatc aggtgaacca attaatattg atgacattat gagttcgaag atatactcta     420
aagtgttatc taaatacaga agacattcgt tcgttctttg cctataactc taaaaggctt     480
gtaacaccct cattcatcct ctatatacga agactctctc ctatcatttt tatcgattta     540
ttttttttat atttagacaa tggaattaaa tagaactaaa atatatataa gatgatatct     600
gaggacccga gatggtaatg gggactcgat cctcgattct ccacggagaa ttcctctagg     660
atataggtaa tttgtcccca cgaggattga acgggtaa tttggtcccc atgtgcccgt       720
cccgcgaact tctcttgatc taaattagtc tatttccatg ttaaaactat actaaaaatt     780
taatacacag tctattataa aatagcaaac taaattctaa agttgatgca tcttgtaatt     840
ttaaatctgg tttgttcaag ttatattcat ttgatataat aaatttgaat ttgactctta     900
atatcgtatt ttttcctaac ggggacggat tctccacggg gataaattcc atgatacaga     960
tgggatgaaa gaaaaatctc ccgtatgaac ttttgcagga atggggatgg ccagagaaa     1020
ttttctccct gcggggacgg gggagccata tcctcggtgg agaatttccc attatcatcc    1080
ttatttgtgg tacatatata tgcataatct tttttttttg actgacatgt gggaaagtat    1140
cccatctcaa tagtagaaaa tcttgggaac ggtaggatcg aacacaaaga tcagctagct    1200
tgtaatcacc gagccatata gctagagggt aatagatcat gaatcaaatg ttttttttcat   1260
aaattattaa ggctctaaat tattttttaat ttaaaaataa ataaaaatat agttcgattc    1320
ttacatttta tagtgtaaaa cttttaaagtc tattattacc cctacttatt gagttatggt    1380
tcagttcttg tcgacggaga gtaatgagat atagaataag gtaccctata gaataaagaa    1440
tctttctctg aaaagtctga cgtacgtaaa taagatataa taaaaaaaat acaaagagaa    1500
gcgctggact ggagatgctc ctatatgcgg caatgcctgt gcttataaat agccacctcg    1560
gtcggcaagg acagatctcc cccaaatcca cccgtcggca cctccgcttc aaggtacgcc    1620
gctcgtcctc cccccccccc cccctctcta ccttctctag atcggcgttc cggtccatgc    1680
atggttaggg cccggtagtt ctacttctgt tcatgtttgt gttagatccg tgtttgtgtt    1740
agatccgtgc tgctagcgtt cgtacacgga tgcgacctgt acgtcagaca cgttctgatt    1800
gctaacttgc cagtgtttct cttttgggaa tcctgggatg gctctagccg ttccgcagac    1860
gggatcgatt tcatgatttt ttttgtttcg ttgcataggg tttggtttgc ccttttcctt    1920
tatttcaata tatgccgtgc acttgttgt cgggtcatct tttcatgctt tttttttgtct    1980
tggttgtgat gatgtggtct ggttgggcgg tcgttctaga tcggagtaga attctgtttc    2040
aaactacctg gtggatttat taattttgga tctgtatgtg tgtgccatac atattcatag    2100
ttacgaattg aagatgatgg atggaaatat cgatctagga taggtataca tgttgatgcg    2160
ggttttactg atgcatatac agagatgctt tttgttcgct tggttgtgat gatgtggtgt    2220
```

```
ggttgggcgg tcgttcattc gttctagatc ggagtagaat actgtttcaa actacctggt    2280
gtatttatta attttggaac tgtatgtgtg tgtcatacat cttcatagtt acgagtttaa    2340
gatggatgga aatatcgatc taggataggt atacatgttg atgtgggttt tactgatgca    2400
tatacatgat ggcatatgca gcatctattc atatgctcta accttgagta cctatctatt    2460
ataataaaca agtatgtttt ataattattt cgatcttgat atacttggat gatggcatat    2520
gcagcagcta tatgtggatt tttttagccc tgccttcata cgctatttat ttgcttggta    2580
ctgtttcttt tgtcgatgct caccctgttg tttggtgtta cttctgcagg tacagtagtt    2640
agttgaggta ccgatccac acgacaccat ggcatctgga gcacttctct ttcatgggaa     2700
gattccttac gttgtggaga tggaagggaa tgttgatggc cacacccttta gcatacgtgg   2760 gaaaggctac ggagatgcct cagtgggaaa ggttgatgca cagttcatct gcacaactgg   2820
tgatgttcct gtgccttgga gcacacttgt caccactctc acctatggag cacagtgctt   2880
tgccaagtat ggtccagagt tgaaggactt ctacaagtcc tgtatgccag atggctatgt   2940
gcaagagcgc acaatcacct ttgaaggaga tggcaacttc aagactaggg ctgaagtcac   3000
ctttgagaat gggtctgtct acaatagggt caaactcaat ggtcaaggct tcaagaaaga   3060
tggtcatgtg ttgggaaaga acttggagtt caacttcact ccccactgcc tctacatctg   3120
gggtgaccaa gccaaccacg gtctcaagtc agccttcaag atctgtcatg agattactgg   3180
cagcaaaggc gacttcatag tggctgacca cacccagatg aacactccca ttggtggagg   3240
tccagttcat gttccagagt atcatcacat gtcttaccat gtgaaacttt ccaaagatgt   3300
gacagaccac agagacaaca tgtccttgaa agaaactgtc agagctgttg actgtcgcaa   3360
gacctacctt tgagtagtta gcttaatcac ctagagctct ctacgagcaa cacgtccact   3420
aggatcagca gctgtcagtg acagataaga taacggcgca attacctaat ctgcgtagta   3480
cgagcagcgg taacctttaa actgagggca ctgaagtcgc ttgatgtgct gaattgtttg   3540
tgatgttggt ggcgtatttt gtttaaataa gtaagcatgg ctgtgatttt atcatatgat   3600
cgatctttgg ggttttattt aacacattgt aaaatgtgta tctattaata actcaatgta   3660
taagatgtgt tcattcttcg gttgccatag atctgcttat ttgacctgtg atgttttgac   3720
tccaaaaacc aaaatcacaa ctcaataaac tcatggaata tgtccacctg tttcttgaag   3780
agttcatcta ccattccagt tggcatttat cagtgttgca gcggcgctgt gctttgtaac   3840
ataacaattg ttacggcata tatccaa                                       3867
```

PLANT PROMOTOR AND 3' UTR FOR TRANSGENE EXPRESSION

CROSS REFERENCE TO RELATED APPLICATION

The present application claims priority to the benefit of U.S. Provisional Patent Application Ser. No. 62/205,756 filed Aug. 17, 2015 the disclosure of which is hereby incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 27.3 KB ACII (Text) file named "77502-US-PSP-20150814-Sequence-ST25.txt" created on Aug. 14, 2015.

BACKGROUND

Many plant species are capable of being transformed with transgenes to introduce agronomically desirable traits or characteristics. The resulting plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation of the plant genome results in transgenic plants that possess desirable traits and phenotypes. However, mechanisms that allow the production of transgenic plant species to highly express multiple transgenes engineered as a trait stack are desirable.

Likewise, mechanisms that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Furthermore, it may be desirable to express a transgene in leaf and stem tissues of a plant to provide tolerance against herbicides, or resistance against above ground insects and pests.

Therefore, a need exists for new gene regulatory elements that can drive the desired levels of expression of transgenes in specific plant tissues.

BRIEF SUMMARY

In embodiments of the subject disclosure, the disclosure relates to a nucleic acid vector comprising a 3' UTR operably linked to a polylinker sequence, a non-*Zea may* Zrp2 gene, or a combination of the polylinker sequence and the non-*Zea may* Zrp2 gene. In such aspects of this embodiment, the 3' UTR comprises a polynucleotide sequence that has at least 90% sequence identity with SEQ ID NO:3. Further embodiments include the 3' UTR comprising a polynucleotide of 500 bp in length. Also included are embodiments to polynucleotides that share 80%, 85%, 90%, 92.5%, 95%, 97.5%, 99%, or 99.9% sequence identity to the 3' UTR of SEQ ID NO:3. Embodiments include the nucleic acid vector, further comprising a sequence encoding a selectable maker. Also considered are embodiments of the nucleic acid vector, wherein said 3' UTR is operably linked to a transgene. Examples of such a transgene include a selectable marker or a gene product conferring insecticidal resistance, herbicide tolerance, nitrogen use efficiency, water use efficiency, or nutritional quality. Further considered are embodiments of the nucleic acid vector, wherein said 3' UTR is operably linked to a RNAi expressing polynucleotide.

In other aspects, the subject disclosure relates to a nucleic acid (or polynucleotide) comprising a promoter polynucleotide sequence that has at least 80%, 85%, 90%, 92.5%, 95%, 97.5%, 99%, and 99.9% sequence identity with SEQ ID NO:1. Accordingly, such a promoter is incorporated into a nucleic acid vector comprising the 3' UTR of SEQ ID NO:3. In aspects of this embodiment the promoter (e.g. SEQ ID NO:1) is operably linked to the 5' end of a polylinker or a transgene, and the 3' UTR is operably linked to the 3' end of a polylinker or a transgene. Further included in this embodiment is a nucleic acid vector, wherein the promoter further comprises an intron or a 5'-UTR. Subsequently, the nucleic acid vector containing the promoter of SEQ ID NO:1 and the 3' UTR of SEQ ID NO:3 drives expression of a transgene with below ground tissue specific expression.

In other aspects, the subject disclosure relates to a nucleic acid (or polynucleotide) comprising a promoter polynucleotide sequence that has at least 80%, 85%, 90%, 92.5%, 95%, 97.5%, 99%, or 99.9% sequence identity with SEQ ID NO:6. Accordingly, such a promoter is incorporated into a nucleic acid vector comprising the 3' UTR of SEQ ID NO:3. In aspects of this embodiment the promoter (e.g., SEQ ID NO:6) is operably linked to the 5' end of a polylinker or a transgene, and the 3' UTR is operably linked to the 3' end of a polylinker or a transgene. Subsequently, the nucleic acid vector containing the promoter of SEQ ID NO:6 and the 3' UTR of SEQ ID NO:3 drives expression of a transgene with below ground tissue specific expression.

In other aspects, the subject disclosure relates to a plant comprising a polynucleotide sequence that has at least 90% sequence identity with SEQ ID NO:3 operably linked to a transgene. Accordingly, the plant is either a monocotyledonous or a dicotyledonous plant. Specific examples of plants include maize, wheat, rice, *sorghum*, oats, rye, bananas, sugar cane, soybean, cotton, *Arabidopsis*, tobacco, sunflower, and canola. In embodiments, such plants may be transformed, wherein the transgene is inserted into the genome of said plant. In additional embodiments, the plant contains a 3' UTR comprising a polynucleotide sequence having at least 80%, 85%, 90%, 92.5%, 95%, 97.5%, 99%, or 99.9% sequence identity with SEQ ID NO:3. In such embodiments, SEQ ID NO:3 is 500 bp in length. In an aspect of this embodiment, the 3' UTR is operably linked to a transgene. In other embodiments, the plant contains a promoter comprising a polynucleotide sequence having at least 80%, 85%, 90%, 92.5%, 95%, 97.5%, 99%, or 99.9% sequence identity with SEQ ID NO:1. In such embodiments, SEQ ID NO:1 is 1,572 bp in length. In an aspect of this embodiment, the promoter of SEQ ID NO:1 is operably linked to a transgene. In other embodiments, the plant contains a promoter comprising a polynucleotide sequence having at least 80%, 85%, 90%, 92.5%, 95%, 97.5%, 99%, or 99.9% sequence identity with SEQ ID NO:6. In an aspect of this embodiment, the promoter of SEQ ID NO:6 is operably linked to a transgene. Furthermore, the embodiments relate to a plant comprising the 3'UTR of SEQ ID NO:1, wherein transgene expression is below ground tissue specific expression. Likewise, the embodiments relate to a plant comprising the 3'UTR of SEQ ID NO:1 and a promoter or SEQ ID NO:1, wherein transgene expression is below ground tissue specific expression.

In other aspects, the subject disclosure relates to a method for producing a transgenic plant cell. Such a method utilizes transforming a plant cell with a gene expression cassette comprising a *Zea mays* Zrp2 3'UTR operably linked to at least one polynucleotide sequence of interest. Next, the method discloses isolating the transformed plant cell comprising the gene expression cassette. Further, the method considers producing a transgenic plant cell comprising the *Zea mays* Zrp2 3'UTR operably linked to at least one polynucleotide sequence of interest. Likewise, the method includes regenerating the transgenic plant cell into a transgenic plant. In addition, the method includes obtaining the transgenic plant, wherein the transgenic plant comprises the gene expression cassette comprising the *Zea mays* Zrp2 3'UTR operably linked to at least one polynucleotide sequence of interest. In such an embodiment, the method of transforming a plant cell is performed with a plant transformation method. In other embodiments, the method of transforming a plant cell results in a polynucleotide sequence of interest that is stably integrated into the genome of the transgenic plant cell. In aspects of such embodiments, the *Zea mays* Zrp2 3'UTR comprises the polynucleotide of SEQ ID NO:3.

In other aspects, the subject disclosure relates to an isolated polynucleotide comprising a nucleic acid sequence with at least 80%, 85%, 90%, 92.5%, 95%, 97.5%, 99%, or 99.9% sequence identity to the polynucleotide of SEQ ID NO:3. In an embodiment, the isolated polynucleotide further comprises an open-reading frame polynucleotide coding for a polypeptide; and a promoter sequence. In another embodiment, the polynucleotide of SEQ ID NO:3 is 500 bp in length.

In embodiments of the subject disclosure, the disclosure relates to a nucleic acid vector comprising a promoter operably linked to: a polylinker sequence; a non-ZmZRP2 like gene; or a combination of the polylinker sequence and the a non-ZmZRP2 like gene, wherein said promoter comprises a polynucleotide sequence that has at least 90% sequence identity with SEQ ID NO:1. In some embodiments, the promoter is 1,572 bp in length. In additional embodiments, the promoter consists of a polynucleotide sequence that has at least 90% sequence identity with SEQ ID NO:1. In other embodiments, the promoter drives expression of a polynucleotide encoding a selectable maker. In further embodiments, the promoter is operably linked to a transgene. In aspects of this embodiment, the transgene encodes a selectable marker or a gene product conferring insecticidal resistance, herbicide tolerance, nitrogen use efficiency, water use efficiency, or nutritional quality. The promoter of SEQ ID NO:1 is provided for use with a 3' untranslated polynucleotide sequence (3'-UTR), the 3' untranslated polynucleotide sequence comprising a sequence that has at least 90% sequence identity with SEQ ID NO:3, wherein the 3' untranslated sequence is operably linked to said polylinker or said transgene. In other embodiments, the promoter of SEQ ID NO:1 is provided for use with an intron polynucleotide sequence, the intron polynucleotide sequence comprising a sequence that has at least 90% sequence identity with SEQ ID NO:2, wherein the intron polynucleotide sequence is operably linked to said polylinker or said transgene. In such aspects of the embodiment, the polynucleotide sequences of SEQ ID NO:1 operably linked to SEQ ID NO:2 comprise SEQ ID NO:6. In a further embodiment, the promoter of SEQ ID NO:1 drives below ground tissue specific expression. In additional embodiments, the promoter of SEQ ID NO:6 drives below ground tissue specific expression.

In yet another embodiment, the subject disclosure provides for a plant comprising a polynucleotide sequence that has at least 90% sequence identity with SEQ ID NO:1 operably linked to a transgene or to a linker sequence. Other aspects of this embodiment include a plant comprising a polynucleotide sequence that has at least 90% sequence identity with SEQ ID NO:6 operably linked to a transgene or to a linker sequence. In accordance with this embodiment, the plant is selected from the group consisting of maize, wheat, rice, *sorghum*, oats, rye, bananas, sugar cane, soybean, cotton, *Arabidopsis*, tobacco, sunflower, and canola. Subsequently, the plant that comprises the polynucleotide sequence that has at least 90% sequence identity with SEQ ID NO:1 may be a *Zea mays* plant in some embodiments. In other embodiments, the transgene is that is operably linked to the polynucleotide sequence that has at least 90% sequence identity with SEQ ID NO:1 is inserted into the genome of a plant. In some embodiments, the polynucleotide sequence having at least 90% sequence identity with SEQ ID NO:1 is a promoter and said promoter is operably linked to a transgene. In other embodiments, the plant comprises a 3' untranslated sequence comprising SEQ ID NO:3 or a 3' untranslated sequence that has at least 90% sequence identity with SEQ ID NO:3, wherein the 3' untranslated sequence is operably linked to a transgene. In an additional embodiment, the polynucleotide sequence that has at least 90% sequence identity with SEQ ID NO:1 drives expression of the transgene with below ground tissue specific expression. In a further embodiment, the polynucleotide sequence that has at least 90% sequence identity with SEQ ID NO:1 is 1,572 bp in length.

In an embodiment, the subject disclosure provides for a method for producing a transgenic plant cell, the method comprising the steps of: transforming a plant cell with a gene expression cassette comprising a *Zea mays* ZRP2 gene promoter operably linked to at least one polynucleotide sequence of interest; isolating the transformed plant cell comprising the gene expression cassette; and, producing a transgenic plant cell comprising the *Zea mays* ZRP2 gene promoter operably linked to at least one polynucleotide sequence of interest. In other embodiments, the step of transforming a plant cell is performed with a plant transformation method. The plant transformation method can be selected from the group consisting of an *Agrobacterium*-mediated transformation method, a biolistics transformation method, a silicon carbide transformation method, a protoplast transformation method, and a liposome transformation method. In other embodiments, the polynucleotide sequence of interest is constitutively expressed throughout the transgenic plant cell. In some embodiments, the polynucleotide sequence of interest is stably integrated into the genome of the transgenic plant cell. Accordingly, the method for producing a transgenic plant cell can further comprise the steps of: regenerating the transgenic plant cell into a transgenic plant; and, obtaining the transgenic plant, wherein the transgenic plant comprises the gene expression cassette comprising the *Zea mays* ZRP2 gene promoter of claim 1 operably linked to at least one polynucleotide sequence of interest. In an embodiment, the transgenic plant cell is a monocotyledonous transgenic plant cell or a dicotyledonous transgenic plant cell. For example, the dicotyledonous transgenic plant cell can be selected from the group consisting of an *Arabidopsis* plant cell, a tobacco plant cell, a soybean plant cell, a canola plant cell, and a cotton plant cell. Further, the monocotyledonous transgenic plant cell is selected from the group consisting of a maize plant cell, a rice plant cell, and a wheat plant cell. The *Zea mays* ZRP2 gene promoter used in the method may comprise the polynucleotide of SEQ ID NO: 1. In other embodiments the *Zea mays* ZRP2 gene promoter used in the method may comprise the polynucleotide of SEQ ID NO:6. In embodiments, the *Zea mays* ZRP2 gene promoter may further comprise a first polynucleotide sequence of interest operably linked to the 3' end of SEQ ID NO: 1.

In an embodiment, the subject disclosure provides for a method for expressing a polynucleotide sequence of interest in a plant cell, the method comprising introducing into the plant cell a polynucleotide sequence of interest operably linked to a *Zea mays* ZRP2 gene promoter. In some embodiments, the polynucleotide sequence of interest operably linked to the *Zea mays* ZRP2 gene promoter is introduced into the plant cell by a plant transformation method. As such, the plant transformation method can be selected from the group consisting of an *Agrobacterium*-mediated transformation method, a biolistics transformation method, a silicon carbide transformation method, a protoplast transformation method, and a liposome transformation method. In embodiments, the polynucleotide sequence of interest is constitutively expressed throughout the plant cell. In some embodiments, the polynucleotide sequence of interest is stably integrated into the genome of the plant cell. As such, the transgenic plant cell is a monocotyledonous plant cell or a dicotyledonous plant cell. As an example, the dicotyledonous plant cell is selected from the group consisting of an *Arabidopsis* plant cell, a tobacco plant cell, a soybean plant cell, a canola plant cell, and a cotton plant cell. Further, the monocotyledonous plant cell is selected from the group consisting of a maize plant cell, a rice plant cell, and a wheat plant cell.

In an embodiment, the subject disclosure provides for a transgenic plant cell comprising a *Zea mays* ZRP2 gene promoter. In some embodiments, the transgenic plant cell comprises a transgenic event. In an aspect of the embodiment, the transgenic event comprises an agronomic trait. Accordingly, the agronomic trait is selected from the group consisting of an insecticidal resistance trait, herbicide tolerance trait, nitrogen use efficiency trait, water use efficiency trait, nutritional quality trait, DNA binding trait, selectable marker trait, small RNA trait, or any combination thereof. In other embodiments, the agronomic trait comprises an herbicide tolerant trait. In an aspect of the embodiment, the herbicide tolerant trait comprises an aad-1 coding sequence. In some embodiments, the transgenic plant cell produces a commodity product. The commodity product is selected protein concentrate, protein isolate, grain, meal, flour, oil, or fiber. In an embodiment, the transgenic plant cell is selected from the group consisting of a dicotyledonous plant cell or a monocotyledonous plant cell. Accordingly, the monocotyledonous plant cell is a maize plant cell. In other embodiments, the *Zea mays* ZRP2 gene promoter comprises a polynucleotide with at least 90% sequence identity to the polynucleotide of SEQ ID NO:1. In another aspect, the *Zea mays* ZRP2 gene promoter comprises a polynucleotide with at least 90% sequence identity to the polynucleotide of SEQ ID NO:6. In yet another embodiment, the *Zea mays* ZRP2 gene promoter is 1,572 bp in length. In further embodiments, the *Zea mays* ZRP2 gene promoter consists of SEQ ID NO:1. In another aspect the *Zea mays* ZRP2 gene promoter consists of SEQ ID NO:6. In additional embodiments, the *Zea mays* ZRP2 gene promoter consists of SEQ ID NO:1 is operably linked to the 3' end of SEQ ID NO:1. In an aspect, the *Zea mays* ZRP2 gene promoter consists of SEQ ID NO:6 is operably linked to the 3' end of SEQ ID NO:6. In other embodiments the *Zea mays* ZRP2 gene promoter drives expression of an agronomic trait in below ground plant tissues.

The subject disclosure provides for an isolated polynucleotide comprising a nucleic acid sequence with at least 90% sequence identity to the polynucleotide of SEQ ID NO:1. Also included are isolated polynucleotides comprising a nucleic acid sequence with at least 90% sequence identity to the polynucleotide of SEQ ID NO:6. In some embodiments, the isolated polynucleotide drives below ground tissue specific expression. In other embodiments, the isolated polynucleotide has expression activity within a plant cell. In embodiments, the isolated polynucleotide comprises an open-reading frame polynucleotide coding for a polypeptide; and a termination sequence. Further embodiments include the isolated polynucleotide comprising a nucleic acid sequence with at least 90% sequence identity to the polynucleotide of SEQ ID NO:1, wherein the polynucleotide of SEQ ID NO:1 is 1,572 bp in length.

The foregoing and other features will become more apparent from the following detailed description of several embodiments, which proceeds with reference to the accompanying figures.

DETAILED DESCRIPTION

I. Overview of Several Embodiments

Figure 1:
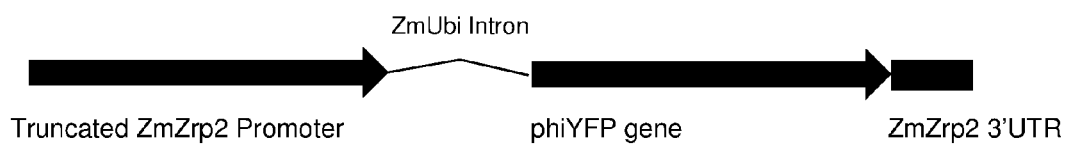
FIG. 1: This figure is a schematic of the gene of interest gene cassette on pDAB113281 which contains the *Zea mays* Zrp2 promoter of SEQ ID NO:1 (labeled as "Truncated ZmZrp2 Promoter") that is operably linked to the *Zea mays* Ubiquitin 1 intron of SEQ ID NO:2 (labeled as "ZmUbi1 Intron") and the *Zea mays* Zrp2 3'-UTR of SEQ ID NO:3 (labeled as "ZmZrp2 3'UTR"). These regulatory elements are operably linked to the phi-yfp gene (labeled as "phiYFP gene").

Development of transgenic plant products is becoming increasingly complex. Commercially viable transgenic plants now require the stacking of multiple transgenes into a single locus. Plant promoters and 3'UTRs used for basic research or biotechnological applications are generally unidirectional, directing only one gene that has been fused at its 3' end (downstream) for the promoter, or at its 5' end (upstream) for the 3' UTR. Accordingly, each transgene usually requires a promoter and 3' UTR for expression, wherein multiple regulatory elements are required to express multiple transgenes within one gene stack. With an increasing number of transgenes in gene stacks, the same promoter and/or 3' UTR is routinely used to obtain similar levels of expression patterns of different transgenes. Obtaining similar levels of transgene expression is necessary for the production of a single polygenic trait. Unfortunately, multigene constructs driven by the same promoter and/or 3' UTR are known to cause gene silencing resulting in less efficacious transgenic products in the field. The repeated promoter and/or 3' UTR elements may lead to homology-based gene silencing. In addition, repetitive sequences within a transgene may lead to gene intra locus homologous recombination resulting in polynucleotide rearrangements. The silencing and rearrangement of transgenes will likely have an undesirable effect on the performance of a transgenic plant produced to express transgenes. Further, excess of transcription factor (TF)-binding sites due to promoter repetition can cause depletion of endogenous TFs leading to transcriptional inactivation. Given the need to introduce multiple genes into plants for metabolic engineering and trait stacking, a variety of promoters and/or 3' UTRs are required to develop transgenic crops that drive the expression of multiple genes.

A particular problem in promoter and/or 3' UTR identification is the need to identify tissue-specific promoters, related to specific cell types, developmental stages and/or functions in the plant that are not expressed in other plant tissues. Tissue specific (i.e., tissue preferred) or organ specific promoters drive gene expression in a certain tissue such as in the kernel, root, leaf, or tapetum of the plant. Tissue and developmental stage specific promoters and/or 3' UTRs can be initially identified from observing the expression of genes, which are expressed in particular tissues or at particular time periods during plant development. These tissue specific promoters and/or 3' UTRs are required for certain applications in the transgenic plant industry and are desirable as they permit specific expression of heterologous genes in a tissue and/or developmental stage selective manner, indicating expression of the heterologous gene differentially at various organs, tissues and/or times, but not in other tissue. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Another application is the desirability of using tissue specific promoters and/or 3' UTRs to confine the expression of the transgenes encoding an agronomic trait in specific tissues types like developing parenchyma cells. As such, a particular problem in the identification of promoters and/or 3' UTRs is how to identify the promoters, and to relate the identified promoter to developmental properties of the cell for specific tissue expression.

Another problem regarding the identification of a promoter is the requirement to clone all relevant cis-acting and trans-activating transcriptional control elements so that the cloned DNA fragment drives transcription in the wanted specific expression pattern. Given that such control elements are located distally from the translation initiation or start site, the size of the polynucleotide that is selected to comprise the promoter is of importance for providing the level of expression and the expression patterns of the promoter polynucleotide sequence. It is known that promoter lengths include functional information, and different genes have been shown to have promoters longer or shorter than promoters of the other genes in the genome. Elucidating the transcription start site of a promoter and predicting the functional gene elements in the promoter region is challenging. Further adding to the challenge are the complexity, diversity and inherent degenerate nature of regulatory motifs and cis- and trans-regulatory elements (Blanchette, Mathieu, et al. "Genome-wide computational prediction of transcriptional regulatory modules reveals new insights into human gene expression." *Genome research* 16.5 (2006): 656-668). The cis- and trans-regulatory elements are located in the distal parts of the promoter which regulate the spatial and temporal expression of a gene to occur only at required sites and at specific times (Porto, Milena Silva, et al. "Plant promoters: an approach of structure and function." *Molecular biotechnology* 56.1 (2014): 38-49). Existing promoter analysis tools cannot reliably identify such cis regulatory elements in a genomic sequence, thus predicting too many false positives because these tools are generally focused only on the sequence content (Fickett J W, Hatzigeorgiou A G (1997) Eukaryotic promoter recognition. Genome research 7: 861-878). Accordingly, the identification of promoter regulatory elements requires that an appropriate sequence of a specific size is obtained that will result in driving expression of an operably linked transgene in a desirable manner.

Provided are methods and compositions for overcoming such problems through the use of *Zea mays* ZRP2 regulatory elements to express transgenes in plantae.

II. Terms and Abbreviations

Throughout the application, a number of terms are used. In order to provide a clear and consistent understanding of the specification and claims, including the scope to be given such terms, the following definitions are provided.

As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendorf™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene is an exogenous nucleic acid, where the transgene sequence has been introduced into a host cell by genetic engineering (or the progeny thereof) where the transgene is not normally found. In one example, a transgene encodes an industrially or pharmaceutically useful compound, or a gene encoding a desirable agricultural trait (e.g., an herbicide-resistance gene). In yet another example, a transgene is an antisense nucleic acid sequence, wherein expression of the antisense nucleic acid sequence inhibits expression of a target nucleic acid sequence. In one embodiment the transgene is an endogenous nucleic acid, wherein additional genomic copies of the endogenous nucleic acid are desired, or a nucleic acid that is in the antisense orientation with respect to the sequence of a target nucleic acid in a host organism.

As used herein the term "non-Zea mays Zrp2 transgene" or "non-Zrp2 gene" is any transgene that has less than 80% sequence identity with the Zea mays Zrp2 transgene gene coding sequence (SEQ ID NO:7 with the Genbank NCBI Accession No. GRMZM2G106980_T02 or SEQ ID NO:8 with the Genbank NCBI Accession No. GRMZM2G106980_T01).

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity as say(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, "homology-based gene silencing" (HBGS) is a generic term that includes both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNAinduced TGS and PTGS likely result from the diversification of an ancient common mechanism. However, a strict comparison of TGS and PTGS has been difficult to achieve because it generally relies on the analysis of distinct silencing loci. In some instances, a single transgene locus can triggers both TGS and PTGS, owing to the production of dsRNA corresponding to promoter and transcribed sequences of different target genes. Mourrain et al. (2007) *Planta* 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual,* 2nd ed., vol. 1-3, Cold Spring Harbor Laboratory Press, Cold Spring Harbor, N.Y., 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

As used herein, the term "sequence identity" or "identity", as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5'-UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) *Genes & Dev.*, 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

As used herein, the terms "5' untranslated region" or "5'-UTR" is defined as the untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the terms "transcription terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

As used herein, the term "3' untranslated region" or "3'-UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3'-UTR is considered to include the polyadenylation signal and transcription terminator.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3); 1457-1468.

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), a RNA molecule (an RNA-binding protein), and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

Examples of DNA binding proteins include; meganucleases, zinc fingers, CRISPRs, and TALE binding domains that can be "engineered" to bind to a predetermined nucleotide sequence. Typically, the engineered DNA binding proteins (e.g., zinc fingers, CRISPRs, or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al., (2007) *Science* 318:648-651). These proteins contain a DNA binding domain and a transcriptional activation domain. One of the most well characterized TAL-effectors is AvrBs3 from *Xanthomonas campestris* pv. *Vesicatoria* (see Bonas et al., (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al., (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al., (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the double-stranded break (DSB) at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) Science 337, pp. 816-821, Jinek et al., (2013), eLife 2:e00471, and David Segal, (2013) eLife 2:e00563). Thus, the CRISPR/Cas system can be engineered to create a DSB at a desired target in a genome, and repair of the DSB can be influenced by the use of repair inhibitors to cause an increase in error prone repair.

In other examples, the DNA binding transgene is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al., (1997) *Nucleic Acids Res.* 25:3379-30 3388; Dujon et al., (1989) *Gene* 82:115-118; Perler et al., (1994) *Nucleic Acids Res.* 22, 11127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al., (2002) *Molec. Cell* 10:895-905; Epinat et al., (2003) *Nucleic Acids Res.* 5 31:2952-2962; Ashworth et al., (2006) *Nature* 441:656-659; Paques et al., (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) Cell 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

An exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the term a transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

As used herein, the terms "Polymerase Chain Reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51:263 (1987); Erlich, ed., PCR Technology, (Stockton Press, N Y, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. Constructs comprising a polylinker are utilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)," "tmRNA" (a.k.a. "10S RNA," Muto et al., (1998) *Trends Biochem Sci.* 23:25-29; and Gillet et al., (2001) *Mol Microbiol.* 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA)," "diced siRNA (d-siRNA)," and aptamers, oligonucleotides and other synthetic nucleic acids that comprise at least one uracil base.

Unless otherwise specifically explained, all technical and scientific terms used herein have the same meaning as commonly understood by those of ordinary skill in the art to which this disclosure belongs. Definitions of common terms in molecular biology can be found in, for example: Lewin, *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

As used herein, the articles, "a," "an," and "the" include plural references unless the context clearly and unambiguously dictates otherwise.

III. *Zea mays* Zrp2 Gene Regulatory Elements and Nucleic Acids Comprising the Same Provided are methods and compositions for using a promoter or a 3' UTR from a *Zea mays* Zrp2 gene to express non-ZmZrp2-like transgenes in plants. In an embodiment, a promoter can be the *Zea mays* Zrp2 gene promoter of SEQ ID NO:1. In a further embodiment, a 3' UTR can be the *Zea mays* Zrp2 gene 3' UTR of SEQ ID NO:3.

In an embodiment, a polynucleotide is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1. In an embodiment, a promoter is a promoter can be the *Zea mays* Zrp2 gene promoter comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:1. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:1. In an embodiment, a nucleic acid vector is provided comprising a promoter can be the *Zea mays* Zrp2 gene promoter of SEQ ID NO: 1. In an embodiment, a polynucleotide is provided comprising a *Zea mays* Zrp2 gene promoter that is operably linked to a polylinker. In an embodiment, a gene expression cassette is provided comprising a *Zea mays* Zrp2 gene promoter that is operably linked to a non-ZmZrp2-like transgene. In an embodiment, a nucleic acid vector is provided comprising a *Zea mays* Zrp2 gene promoter that is operably linked to a non-ZmZrp2 transgene. In one embodiment, the promoter consists of SEQ ID NO: 1. In an illustrative embodiment, a nucleic acid vector comprises a *Zea mays* Zrp2 gene promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

Transgene expression may also be regulated by the 3' untranslated gene region (i.e., 3' UTR) located downstream of the gene's coding sequence. Both a promoter and a 3' UTR can regulate transgene expression. While a promoter is necessary to drive transcription, a 3' UTR gene region can terminate transcription and initiate polyadenylation of a resulting mRNA transcript for translation and protein synthesis. A 3' UTR gene region aids stable expression of a transgene.

In an embodiment, a nucleic acid vector is provided comprising a *Zea mays* Zrp2 gene promoter as described herein and a 3' UTR. In an embodiment, the nucleic acid vector comprises a *Zea mays* Zrp2 gene 3' UTR. In an embodiment, the *Zea mays* Zrp2 gene 3' UTR is SEQ ID NO:3. In an embodiment, the *Zea mays* Zrp2 gene 3' UTR is SEQ ID NO:3.

In an embodiment, a nucleic acid vector is provided comprising a *Zea mays* Zrp2 gene promoter as described herein and a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to the polynucleotide of SEQ ID NO:3. In an embodiment, a nucleic acid vector is provided comprising a 3' UTR wherein the *Zea mays* Zrp2 3' UTR is operably linked to the 3' end of a polylinker. In an embodiment, a gene expression cassette is provided comprising a 3' UTR, wherein the *Zea mays* Zrp2 gene 3' UTR is operably linked to the 3' end of a non-ZmZrp2 transgene.

In one embodiment the 3'-UTR, consists of SEQ ID NO:3. In one embodiment, a gene expression cassette is provided comprising a *Zea mays* Zrp2 3'-UTR, wherein the *Zea mays* Zrp2 3'-UTR comprises SEQ ID NO: 3, and wherein the 3'-UTR is operably linked to the 3' end of a non-ZmZrp2 transgene. In an aspect of this embodiment the 3'-UTR, consists of SEQ ID NO:3. In an illustrative embodiment, a gene expression cassette comprises a *Zea mays* Zrp2 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a small RNA transgene, a selectable marker transgene, or combinations thereof. In a further embodiment the transgene is operably linked to a *Zea mays* Zrp2 3'-UTR from a ZmZrp2 gene of SEQ ID NO:7 or SEQ ID NO:8.

In another embodiment, a nucleic acid vector is provided comprising a *Zea mays* Zrp2 gene promoter as described herein and a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to the polynucleotide of SEQ ID NO:3. In an embodiment, a nucleic acid vector is provided comprising a *Zea mays* Zrp2 gene promoter as described herein and the 3' UTR wherein the *Zea mays* Zrp2 gene promoter and 3' UTR are both operably linked to opposite ends of a polylinker. In an embodiment, a gene expression cassette is provided comprising a *Zea mays* Zrp2 gene promoter as described herein and a 3' UTR, wherein the *Zea mays* Zrp2 gene promoter and 3' UTR are both operably linked to opposite ends of a non-ZmZrp2 transgene. In one embodiment the 3'-UTR, consists of SEQ ID NO:3. In one embodiment, a gene expression cassette is provided comprising a *Zea mays* Zrp2 gene promoter as described herein and a 3'-UTR, wherein the *Zea mays* Zrp2 gene promoter comprises SEQ ID NO: 1 and the 3'-UTR comprises SEQ ID NO: 3 wherein the promoter and 3'-UTR are operably linked to opposite ends of a non-ZmZrp2 transgene. In an aspect of this embodiment the 3'-UTR, consists of SEQ ID NO:3. In another aspect of this embodiment the promoter consists of SEQ ID NO: 1. In an illustrative embodiment, a gene expression cassette comprises a *Zea mays* Zrp2 gene 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a small RNA transgene, a selectable marker transgene, or combinations thereof. In a further embodiment the transgene is operably linked to a *Zea mays* Zrp2 gene promoter and a 3'-UTR from the same ZmZrp2 gene.

Transgene expression may also be regulated by an intron region located downstream of the promoter sequence. Both a promoter and an intron can regulate transgene expression. While a promoter is necessary to drive transcription, the presence of an intron can increase expression levels resulting in mRNA transcript for translation and protein synthesis. An intron gene region aids stable expression of a transgene. In a further embodiment an intron is operably linked to a *Zea mays* Zrp2 gene promoter.

In an embodiment, a nucleic acid construct is provided comprising a *Zea mays* Zrp2 gene promoter as disclosed herein and an intron, wherein the intron is at least 80%, 85%, 90%, 91%, 92%, 93%, 94%, 95%, 96%, 97%, 98%, 99%, 99.5%, 99.8%, or 100% identical to SEQ ID NO:2. In an embodiment, a nucleic acid construct is provided comprising *Zea mays* Zrp2 gene promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1 and a *Zea mays* Ubiquitin 1 intron of SEQ ID NO:2 operably linked to a polylinker. In an embodiment, a gene expression cassette is provided comprising a *Zea mays* Zrp2 gene promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, and a *Zea mays* Ubiquitin 1 intron sequence of SEQ ID NO:2 operably linked to a non-ZmZrp2 transgene. Optionally, the construct can further comprise an 3' UTR that is operably linked to the 3' end of the non-ZmZrp2 transgene. In one embodiment the promoter and 3'-UTR sequences are selected from those described herein and the intron sequence consists of SEQ ID NO:2. In one embodiment the 3'-UTR consists of SEQ ID NO:3.

In an embodiment, a nucleic acid vector is provided comprising a *Zea mays* Zrp2 gene promoter as described herein, a *Zea mays* Ubiquitin 1 intron, and a 3'-UTR, wherein the *Zea mays* Ubiquitin 1 intron is at least 80%, 85%, 90%, 91%, 92%, 93%, 94%, 95%, 96%, 97%, 98%, 99%, 99.5%, 99.8%, or 100% identical to the polynucleotide of SEQ ID NO:2. In an embodiment, a nucleic acid vector is provided comprising a *Zea mays* Zrp2 gene promoter as described herein and the *Zea mays* Ubiquitin 1 intron wherein the *Zea mays* Zrp2 gene promoter and *Zea mays* Ubiquitin 1 intron are both operably linked to one another and comprise SEQ ID NO:6. In an embodiment, a nucleic acid vector is provided comprising a *Zea mays* Zrp2 gene promoter as described herein and the *Zea mays* Ubiquitin 1 intron wherein the *Zea mays* Zrp2 gene promoter and *Zea mays* Ubiquitin 1 intron of SEQ ID NO:6 are both operably linked to a polylinker. In an embodiment, a gene expression cassette is provided comprising a *Zea mays* Zrp2 gene promoter as described herein, an *Zea mays* Ubiquitin 1 intron and a 3'-UTR, wherein the *Zea mays* Zrp2 gene promoter and *Zea mays* Ubiquitin 1 intron are operably linked to the 5' end of a non-ZmZrp2 transgene, and the 3'-UTR is operably linked to the 3' end of a non-ZmZrp2 transgene. In one embodiment the *Zea mays* Ubiquitin 1 intron, consists of SEQ ID NO:2. In one embodiment, a gene expression cassette is provided comprising a *Zea mays* Zrp2 gene promoter as described herein and a *Zea mays* Ubiquitin 1 intron, wherein the *Zea mays* Zrp2 gene promoter comprises SEQ ID NO: 1 and the *Zea mays* Ubiquitin 1 intron comprises SEQ ID NO: 2 and the combination comprises SEQ ID NO:6 wherein the promoter and intron are operably linked to the 5' end of a non-ZmZrp2 transgene. In an aspect of this embodiment the intron, consists of SEQ ID NO:2. In another aspect of this embodiment the promoter consists of SEQ ID NO: 1. In an illustrative embodiment, a gene expression cassette comprises a *Zea mays* Ubiquitin 1 intron that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a small RNA transgene, a selectable marker transgene, or combinations thereof. In a further embodiment the transgene is operably linked to a *Zea mays* Zrp2 gene promoter and a *Zea mays* Ubiquitin 1 intron.

A *Zea mays* Zrp2 gene promoter may also comprise one or more additional sequence elements. In some embodiments, a *Zea mays* Zrp2 gene promoter may comprise an exon (e.g., a leader or signal peptide such as a chloroplast transit peptide or ER retention signal). For example and without limitation, a *Zea mays* Zrp2 gene promoter may encode an exon incorporated into the *Zea mays* Zrp2 gene promoter as a further embodiment.

In an embodiment, a nucleic acid vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

In accordance with one embodiment a nucleic acid vector is provided comprising a recombinant gene expression cassette wherein the recombinant gene expression cassette comprises a *Zea mays* Zrp2 gene promoter operably linked to a polylinker sequence, a non-ZmZrp2 transgene or combination thereof. In one embodiment the recombinant gene cassette comprises a *Zea mays* Zrp2 gene promoter operably linked to a non-ZmZrp2 transgene. In one embodiment the recombinant gene cassette comprises a *Zea mays* Zrp2 gene promoter as disclosed herein is operably linked to a polylinker sequence. The polylinker is operably linked to the *Zea mays* Zrp2 gene promoter in a manner such that insertion of a coding sequence into one of the restriction sites of the polylinker will operably link the coding sequence allowing for expression of the coding sequence when the vector is transformed or transfected into a host cell.

In accordance with one embodiment the *Zea mays* Zrp2 gene promoter comprises SEQ ID NO: 1 or a sequence that has 80, 85, 90, 95 or 99% sequence identity with SEQ ID NO: 1. In accordance with one embodiment the promoter sequence has a total length of no more than 1.5, 2, 2.5, 3 or 4 kb. In accordance with one embodiment the *Zea mays* Zrp2 gene promoter consists of SEQ ID NO: 1 or a 1,572 bp sequence that has 80, 85, 90, 95 or 99% sequence identity with SEQ ID NO: 1.

In accordance with one embodiment a nucleic acid vector is provided comprising a gene cassette that consists of a *Zea mays* Zrp2 gene promoter, a non-ZmZrp2 transgene and a *Zea mays* Zrp2 gene 3'-UTR of SEQ ID NO: 3. In an embodiment, the *Zea mays* Zrp2 gene 3'-UTR of SEQ ID NO: 3 is operably linked to the 3' end of the non-ZmZrp2 transgene. In a further embodiment the 3' untranslated sequence comprises SEQ ID NO: 3 or a sequence that has 80, 85, 90, 95, 99 or 100% sequence identity with SEQ ID NO: 3. In accordance with one embodiment a nucleic acid vector is provided comprising a gene cassette that consists of SEQ ID NO: 1, or a 1,572 bp sequence that has 80, 85, 90, 95, or 99% sequence identity with SEQ ID NO: 1, a non-ZmZrp2 transgene and a 3' UTR, wherein SEQ ID NO: 1 is operably linked to the 5' end of the non-ZmZrp2 transgene and the 3' UTR of SEQ ID NO:3 is operably linked to the 3' end of the non-ZmZrp2 transgene. In a further embodiment the 3' untranslated sequence comprises SEQ ID NO: 3 or a sequence that has 80, 85, 90, 95, 99 or 100% sequence identity with SEQ ID NO: 3. In a further embodiment the 3' untranslated sequence consists of SEQ ID NO: 3, or a 500 bp sequence that has 80, 85, 90, 95, or 99% sequence identity with SEQ ID NO: 3.

In accordance with one embodiment a nucleic acid vector is provided comprising a gene cassette that consists of a *Zea mays* Zrp2 gene promoter, a *Zea mays* Ubiquitin 1 intron of SEQ ID NO:2, a non-ZmZrp2 transgene and a *Zea mays* Zrp2 gene 3'-UTR of SEQ ID NO: 3. In an embodiment, the *Zea mays* Ubiquitin 1 intron of SEQ ID NO: 2 is operably linked to the 5' end of the non-ZmZrp2 transgene and the 3' end of the *Zea mays* Zrp2 gene promoter of SEQ ID NO: 1. In a further embodiment the *Zea mays* Ubiquitin 1 intron sequence comprises SEQ ID NO: 2 or a sequence that has 80, 85, 90, 95, 99 or 100% sequence identity with SEQ ID NO:2. In accordance with one embodiment a nucleic acid vector is provided comprising a gene cassette that consists of SEQ ID NO:2, or a 1,057 bp sequence that has 80, 85, 90, 95, or 99% sequence identity with SEQ ID NO:2, a promoter, a non-ZmZrp2 transgene and a 3'-UTR, wherein SEQ ID NO:1 is operably linked to the 5' end of the *Zea mays* Ubiquitin 1 intron region, and the *Zea mays* Ubiquitin 1 intron is operably linked to the 3' end of the non-ZmZrp2 transgene and the 3'-UTR of SEQ ID NO:3 is operably linked to the 3' end of the non-ZmZrp2 transgene. In a further embodiment the *Zea mays* Ubiquitin 1 intron sequence comprises SEQ ID NO:2 or a sequence that has 80, 85, 90, 95, 99 or 100% sequence identity with SEQ ID NO:2. In a further embodiment the *Zea mays* Ubiquitin 1 intron sequence consists of SEQ ID NO:2, or a 1,057 bp sequence that has 80, 85, 90, 95, or 99% sequence identity with SEQ ID NO:2.

In one embodiment a nucleic acid construct is provided comprising a promoter and a non-ZmZrp2 transgene and optionally one or more of the following elements:
  a) a 5' untranslated region;
  b) an intron; and
  c) a 3' untranslated region,
wherein,
  the promoter consists of SEQ ID NO:1 or a sequence having 98% sequence identity with SEQ ID NO:1;
  the intron region consists of SEQ ID NO:2 or a sequence having 98% sequence identity with SEQ ID NO:2; and
  the 3' untranslated region consists of SEQ ID NO:3 or a sequence having 98% sequence identity with SEQ ID NO:3;
further wherein said promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In one embodiment a nucleic acid construct is provided comprising a promoter and a non-ZmZrp2 transgene and optionally one or more of the following elements:
  a) a intron; and
  b) a 3' untranslated region,
wherein,
  the promoter consists of SEQ ID NO:1 or a sequence having 98% sequence identity with SEQ ID NO:1;
  the intron region consists of SEQ ID NO:2 or a sequence having 98% sequence identity with SEQ ID NO:2; and
  the 3' untranslated region consists of SEQ ID NO:3 or a sequence having 98% sequence identity with SEQ ID NO:3;
further wherein said promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In accordance with one embodiment the nucleic acid vector further comprises a sequence encoding a selectable maker. In accordance with one embodiment the recombinant gene cassette is operably linked to an *Agrobacterium* T-DNA border. In accordance with one embodiment the recombinant gene cassette further comprises a first and second T-DNA border, wherein the first T-DNA border is operably linked to one end of the gene construct, and the second T-DNA border is operably linked to the other end of the gene construct. The first and second *Agrobacterium* T-DNA borders can be independently selected from T-DNA border sequences originating from bacterial strains selected from the group consisting of a nopaline synthesizing *Agrobacterium* T-DNA border, an octopine synthesizing *Agrobacterium* T-DNA border, a mannopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene operably linked to a sequence selected from SEQ ID NO:6 or a sequence having 80, 85, 90, 95, or 99% sequence identity with SEQ ID NO:6.

Transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene encodes a selectable marker or a gene product conferring insecticidal resistance, herbicide tolerance, small RNA expression, nitrogen use efficiency, water use efficiency, or nutritional quality.

1. Insect Resistance

Various insect resistance coding sequences can be operably linked to the *Zea mays* Zrp2 gene promoter comprising SEQ ID NO: 1, or a sequence that has 80, 85, 90, 95 or 99% sequence identity with SEQ ID NO: 1. In some embodiments, the sequences are operably linked to the *Zea mays* Zrp2 gene promoter comprising SEQ ID NO: 1 and the *Zea mays* Ubiquitin 1 intron comprising SEQ ID NO: 2, or a sequence that has 80, 85, 90, 95 or 99% sequence identity with SEQ ID NO: 1 operably linked to SEQ ID NO:2 (e.g., SEQ ID NO:6). The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry/Ab (truncated); cry1Ab-Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A(a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance coding sequences can be operably linked to the *Zea mays* Zrp2 gene promoter comprising SEQ ID NO: 1, or a sequence that has 80, 85, 90, 95 or 99% sequence identity with SEQ ID NO: 1. In some embodiments, the sequences are operably linked to the *Zea mays* Zrp2 gene promoter comprising SEQ ID NO: 1 and the *Zea mays* Ubiquitin 1 intron comprising SEQ ID NO: 2, or a sequence that has 80, 85, 90, 95 or 99% sequence identity with SEQ ID NO: 1 operably linked to SEQ ID NO:2 (e.g., SEQ ID NO:6). The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF_W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83.), the *B. subtilis* PPO gene (Li, X. and Nicholl D. 2005. Development of PPO inhibitor-resistant cultures and crops. Pest Manag. Sci. 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. Biosci Biotechnol Biochem 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), 1s+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait coding sequences can be operably linked to the *Zea mays* Zrp2 gene promoter comprising SEQ ID NO: 1, or a sequence that has 80, 85, 90, 95 or 99% sequence identity with SEQ ID NO: 1. In some embodiments, the sequences are operably linked to the *Zea mays* Zrp2 gene promoter comprising SEQ ID NO: 1 and the *Zea mays* Ubiquitin 1 intron comprising SEQ ID NO: 2, or a sequence that has 80, 85, 90, 95 or 99% sequence identity with SEQ ID NO: 1 operably linked to SEQ ID NO:2 (e.g., SEQ ID NO:6). The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding protein coding sequences can be operably linked to the *Zea mays* Zrp2 gene promoter comprising SEQ ID NO: 1, or a sequence that has 80, 85, 90, 95 or 99% sequence identity with SEQ ID NO: 1. In some embodiments, the sequences are operably linked to the *Zea mays* Zrp2 gene promoter comprising SEQ ID NO: 1 and the *Zea mays* Ubiquitin 1 intron comprising SEQ ID NO: 2, or a sequence that has 80, 85, 90, 95 or 99% sequence identity with SEQ ID NO: 1 operably linked to SEQ ID NO:2 (e.g., SEQ ID NO:6). The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, Talens, CRISPRS, and meganucleases. The above list of DNA binding protein coding sequences is not meant to be limiting. Any DNA binding protein coding sequences is encompassed by the present disclosure.

5. Small RNA

Various small RNAs can be operably linked to the *Zea mays* Zrp2 gene promoter comprising SEQ ID NO: 1, or a sequence that has 80, 85, 90, 95 or 99% sequence identity with SEQ ID NO: 1. In some embodiments, the sequences are operably linked to the *Zea mays* Zrp2 gene promoter comprising SEQ ID NO: 1 and the *Zea mays* Ubiquitin 1 intron comprising SEQ ID NO: 2, or a sequence that has 80, 85, 90, 95 or 99% sequence identity with SEQ ID NO: 1 operably linked to SEQ ID NO:2 (e.g., SEQ ID NO:6). The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be operably linked to the *Zea mays* Zrp2 gene promoter comprising SEQ ID NO: 1, or a sequence that has 80, 85, 90, 95 or 99% sequence identity with SEQ ID NO: 1. In some embodiments, the sequences are operably linked to the *Zea mays* Zrp2 gene promoter comprising SEQ ID NO: 1 and the *Zea mays* Ubiquitin 1 intron comprising SEQ ID NO: 2, or a sequence that has 80, 85, 90, 95 or 99% sequence identity with SEQ ID NO: 1 operably linked to SEQ ID NO:2 (e.g., SEQ ID NO:6). The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), red fluorescent protein (DsRFP, RFP, etc), β-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, or transgene is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166,302, and 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); Agrobacterium-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al. (1987) Nature 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-Agrobacterium bacteria or viruses such as Rhizobium sp. NGR234, Sinorhizoboium meliloti, Mesorhizobium loti, potato virus X, cauliflower mosaic virus and cassava vein mosaic virus and/or tobacco mosaic virus, See, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming Brassica plants in particular are described, for example, in U.S. Pat. No. 5,750,871; techniques for transforming soy bean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

Molecular Confirmation

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Such selection and screening methodologies are well known to those skilled in the art. Molecular confirmation methods that can be used to identify transgenic plants are known to those with skill in the art. Several exemplary methods are further described below.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar® assays are a method of detecting and quantifying the presence of a DNA sequence. Briefly, the genomic DNA sample comprising the integrated gene expression cassette polynucleotide is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. In one embodiment, a second fluorescent DNA dye is SYTO13® used at less than 10 μM, less than 4 μM, or less than 2.7 μM.

In further embodiments, Next Generation Sequencing (NGS) can be used for detection. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX™ from 454 Life Sciences/Roche, the Illumina Genome Analyser™ from Solexa and Applied Biosystems' SOLiD™ (acronym for: 'Sequencing by Oligo Ligation and Detection'). In addition, there are two single molecule sequencing methods that are currently being developed. These include the true Single Molecule Sequencing (tSMS) from Helicos Bioscience™ and the Single Molecule Real Time™ sequencing (SMRT) from Pacific Biosciences.

The Genome Sequencher FLX™ which is marketed by 454 Life Sciences/Roche is a long read NGS, which uses emulsion PCR and pyrosequencing to generate sequencing reads. DNA fragments of 300-800 bp or libraries containing fragments of 3-20 kb can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser™ which is marketed by Solexa™ is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems™ is a short read technology. This NGS technology uses fragmented double stranded DNA that are up to 10 kb in length. The system uses sequencing by ligation of dye-labelled oligonucleotide primers and emulsion PCR to generate one billion short reads that result in a total sequence output of up to 30 gigabases per run.

tSMS of Helicos Bioscience™ and SMRT of Pacific Biosciences™ apply a different approach which uses single DNA molecules for the sequence reactions. The tSMS Helicos™ system produces up to 800 million short reads that result in 21 gigabases per run. These reactions are completed using fluorescent dye-labelled virtual terminator nucleotides that is described as a 'sequencing by synthesis' approach.

The SMRT Next Generation Sequencing system marketed by Pacific Biosciences™ uses a real time sequencing by synthesis. This technology can produce reads of up to 1,000 bp in length as a result of not being limited by reversible terminators. Raw read throughput that is equivalent to one-fold coverage of a diploid human genome can be produced per day using this technology.

In another embodiment, the detection can be completed using blotting assays, including Western blots, Northern blots, and Southern blots. Such blotting assays are commonly used techniques in biological research for the identification and quantification of biological samples. These assays include first separating the sample components in gels by electrophoresis, followed by transfer of the electrophoretically separated components from the gels to transfer membranes that are made of materials such as nitrocellulose, polyvinylidene fluoride (PVDF), or Nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers.

In a further embodiment the detection can be completed using an ELISA assay, which uses a solid-phase enzyme immunoassay to detect the presence of a substance, usually an antigen, in a liquid sample or wet sample. Antigens from the sample are attached to a surface of a plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate.

Transgenic Plants

In an embodiment, a plant, plant tissue, or plant cell comprises a *Zea mays* Zrp2 gene promoter. In one embodiment a plant, plant tissue, or plant cell comprises the *Zea mays* Zrp2 gene promoter of a sequence selected from SEQ ID NO:1 or a sequence that has 80%, 85%, 90%, 95% or 99.5% sequence identity with a sequence selected from SEQ ID NO:1. In another embodiment a plant, plant tissue, or plant cell comprises the *Zea mays* Zrp2 gene 3'-UTR comprises a sequence selected from SEQ ID NO:3 or a sequence that has 80%, 85%, 90%, 95% or 99.5% sequence identity with a sequence selected from SEQ ID NO:3. In another embodiment a plant, plant tissue, or plant cell comprises the *Zea mays* Zrp2 gene promoter from SEQ ID NO:1 operably linked to the *Zea mays* Ubiquitin 1 intron comprises a sequence selected from SEQ ID NO:2 or a sequence that has 80%, 85%, 90%, 95% or 99.5% sequence identity with a sequence selected from SEQ ID NO:2. In an embodiment, a plant, plant tissue, or plant cell comprises a gene expression cassette comprising a sequence selected from SEQ ID NO:1, or a sequence that has 80%, 85%, 90%, 95% or 99.5% sequence identity with a sequence selected from SEQ ID NO:1 that is operably linked to a non-ZmZrp2 transgene. In an illustrative embodiment, a plant, plant tissue, or plant cell comprises a gene expression cassette comprising a *Zea mays* Zrp2 gene promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a *Zea mays* Zrp2 gene derived promoter sequence operably linked to a transgene, wherein the *Zea mays* Zrp2 gene derived promoter sequence comprises a sequence SEQ ID NO:1 or a sequence having 80%, 85%, 90%, 95% or 99.5% sequence identity with SEQ ID NO: 1. In one embodiment a plant, plant tissue, or plant cell is provided wherein the plant, plant tissue, or plant cell comprises SEQ ID NO: 1, or a sequence that has 80%, 85%, 90%, 95% or 99.5% sequence identity with SEQ ID NO: 1 operably linked to a non-ZmZrp2 transgene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of maize, wheat, rice, *sorghum*, oats, rye, bananas, sugar cane, soybean, cotton, sunflower, and canola. In one embodiment the plant is *Zea mays*. In accordance with one embodiment the plant, plant tissue, or plant cell comprises SEQ ID NO: 1 or a sequence having 80%, 85%, 90%, 95% or 99.5% sequence identity with SEQ ID NO:1 operably linked to a non-ZmZrp2 transgene. In one embodiment the plant, plant tissue, or plant cell comprises a promoter operably linked to a transgene wherein the promoter consists of SEQ ID NO: 1 or a sequence having 80%, 85%, 90%, 95% or 99.5% sequence identity with SEQ ID NO:1. In accordance with one embodiment the gene construct comprising *Zea mays* Zrp2 gene promoter sequence operably linked to a transgene is incorporated into the genome of the plant, plant tissue, or plant cell.

In an embodiment, a plant, plant tissue, or plant cell according to the methods disclosed herein can be a dicotyledonous plant. The dicotyledonous plant, plant tissue, or plant cell can be, but not limited to alfalfa, rapeseed, canola, Indian mustard, Ethiopian mustard, soybean, sunflower, cotton, beans, broccoli, cabbage, cauliflower, celery, cucumber, eggplant, lettuce; melon, pea, pepper, peanut, potato, pumpkin, radish, spinach, sugarbeet, sunflower, tobacco, tomato, and watermelon.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

The present disclosure also encompasses seeds of the transgenic plants described above, wherein the seed has the transgene or gene construct containing the gene regulatory elements of the subject disclosure. The present disclosure further encompasses the progeny, clones, cell lines or cells of the transgenic plants described above wherein said progeny, clone, cell line or cell has the transgene or gene construct containing the gene regulatory elements of the subject disclosure.

The present disclosure also encompasses the cultivation of transgenic plants described above, wherein the transgenic plant has the transgene or gene construct containing the gene regulatory elements of the subject disclosure. Accordingly, such transgenic plants may be engineered to, inter alia, have one or more desired traits or transgenic events containing the gene regulatory elements of the subject disclosure, by being transformed with nucleic acid molecules according to the invention, and may be cropped or cultivated by any method known to those of skill in the art.

Method of Expressing a Transgene

In an embodiment, a method of expressing at least one transgene in a plant comprises growing a plant comprising a *Zea mays* Zrp2 gene promoter operably linked to at least one transgene or a polylinker sequence. In an embodiment, a method of expressing at least one transgene in a plant comprising growing a plant comprising a *Zea mays* Ubiquitin 1 intron operably linked to at least one transgene or a polylinker sequence. In an embodiment, a method of expressing at least one transgene in a plant comprising growing a plant comprising a *Zea mays* Zrp2 gene 3'-UTR operably linked to at least one transgene or a polylinker sequence. In one embodiment the *Zea mays* Zrp2 gene promoter consists of a sequence selected from SEQ ID NO:1 or a sequence that has 80%, 85%, 90%, 95% or 99.5% sequence identity with a sequence selected from SEQ ID NO: 1. In another embodiment the *Zea mays* Ubiquitin 1 intron consists of a sequence selected from SEQ ID NO:2 or a sequence that has 80%, 85%, 90%, 95% or 99.5% sequence identity with a sequence selected from SEQ ID NO:2. In another embodiment the *Zea mays* Zrp2 gene 3'-UTR consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene in a plant comprising growing a plant comprising a *Zea mays* Zrp2 gene promoter and a *Zea mays* Zrp2 gene 3'-UTR operably linked to at least one transgene. In an embodiment, a method of expressing at least one transgene in a plant comprising growing a plant comprising a *Zea mays* Zrp2 gene promoter and a *Zea mays* Ubiquitin 1 intron operably linked to at least one transgene. In an embodiment, a method of expressing at least one transgene in a plant tissue or plant cell comprising culturing a plant tissue or plant cell comprising a *Zea mays* Zrp2 gene promoter operably linked to at least one transgene. In an embodiment, a method of expressing at least one transgene in a plant tissue or plant cell comprising culturing a plant tissue or plant cell comprising a *Zea mays* Zrp2 gene promoter and a 3'-UTR operably linked to at least one transgene. In an embodiment, a method of expressing at least one transgene in a plant tissue or plant cell comprising culturing a plant tissue or plant cell comprising a *Zea mays* Zrp2 gene promoter and a *Zea mays* Ubiquitin 1 intron operably linked to at least one transgene. In an embodiment, a method of expressing at least one transgene in a plant tissue or plant cell comprising culturing a plant tissue or plant cell comprising a *Zea mays* Zrp2 gene promoter and a *Zea mays* Zrp2 gene 3'-UTR operably linked to at least one transgene. In an embodiment, a method of expressing at least one transgene in a plant tissue or plant cell comprising culturing a plant tissue or plant cell comprising a *Zea mays* Zrp2 gene promoter and a *Zea mays* Ubiquitin 1 intron operably linked to at least one transgene.

In an embodiment, a method of expressing at least one transgene in a plant comprises growing a plant comprising a gene expression cassette comprising a *Zea mays* Zrp2 gene promoter operably linked to at least one transgene. In one embodiment the *Zea mays* Zrp2 gene promoter consists of a sequence selected from SEQ ID NO:1 or a sequence that has 80%, 85%, 90%, 95% or 99.5% sequence identity with a sequence selected from SEQ ID NO: 1. In another embodiment the *Zea mays* Zrp2 gene 3'-UTR consists of a sequence selected from SEQ ID NO:3 or a sequence that has 80%, 85%, 90%, 95% or 99.5% sequence identity with a sequence selected from SEQ ID NO:3. In another embodiment the *Zea mays* Zrp2 gene promoter and the *Zea mays* Ubiquitin 1 intron consists of a sequence selected from SEQ ID NO:6 or a sequence that has 80%, 85%, 90%, 95% or 99.5% sequence identity with a sequence selected from SEQ ID NO:6. In an embodiment, a method of expressing at least one transgene in a plant comprises growing a plant comprising a gene expression cassette comprising a *Zea mays* Zrp2 gene promoter and a *Zea mays* Zrp2 gene 3'-UTR operably linked to at least one transgene. In an embodiment, a method of expressing at least one transgene in a plant comprises growing a plant comprising a gene expression cassette comprising a *Zea mays* Zrp2 gene promoter and a *Zea mays* Ubiquitin 1 intron operably linked to at least one transgene. In an embodiment, a method of expressing at least one transgene in a plant comprises growing a plant comprising a gene expression cassette comprising a *Zea mays* Zrp2 gene 3'-UTR operably linked to at least one transgene. In an embodiment, a method of expressing at least one transgene in a plant comprises growing a plant comprising a gene expression cassette comprising a *Zea mays* Zrp2 gene promoter and the *Zea mays* Ubiquitin 1 intron (SEQ ID NO:6) operably linked to at least one transgene. In an embodiment, a method of expressing at least one transgene in a plant tissue or plant cell comprises culturing a plant tissue or plant cell comprising a gene expression cassette containing a *Zea mays* Zrp2 gene promoter operably linked to at least one transgene. In an embodiment, a method of expressing at least one transgene in a plant tissue or plant cell comprises culturing a plant tissue or plant cell comprising a gene expression cassette containing a *Zea mays* Zrp2 gene 3'-UTR operably linked to at least one transgene. In an embodiment, a method of expressing at least one transgene in a plant tissue or plant cell comprises culturing a plant tissue or plant cell comprising a gene expression cassette containing a *Zea mays* Zrp2 gene promoter and the *Zea mays* Ubiquitin 1 intron (SEQ ID NO:6) operably linked to at least one transgene. In an embodiment, a method of expressing at least one transgene in a plant tissue or plant cell comprises culturing a plant tissue or plant cell comprising a gene expression cassette, a *Zea mays* Zrp2 gene promoter and a *Zea mays* Zrp2 gene 3'-UTR operably linked to at least one transgene. In an embodiment, a method of expressing at least one transgene in a plant tissue or plant cell comprises culturing a plant tissue or plant cell comprising a gene expression cassette, a *Zea mays* Zrp2 gene promoter and the *Zea mays* Ubiquitin 1 intron (SEQ ID NO:6) operably linked to at least one transgene.

The following examples are provided to illustrate certain particular features and/or embodiments. The examples should not be construed to limit the disclosure to the particular features or embodiments exemplified.

EXAMPLES

Example 1: Novel Design of a Combination of Optimized Regulatory Elements from a *Zea mays* Zrp2 Gene The modified promoter from a *Zea mays* Zrp2 gene (SEQ ID NO:1) is a 1,572 bp polynucleotide sequence that was modified by truncating the 5' end of the original version of the promoter sequence (Held et al., 1997; U.S. Pat. No. 5,633,363). In silico analysis of the originally reported and patented nucleotide sequence for the ZmZrp2 promoter identified the presence of repetitive sequence regions corresponding to transposable elements within the 5' end of the promoter region. Since the significant majority of genomic insertions and rearrangements resulting from transposable elements have been reported to result in activation of host suppression systems involving small RNA targeting, DNA methylation and transcriptional gene silencing (Hollister et al., 2011; Lisch and Bennetzen, 2011; and Ito 2012), the novel modified polynucleotide sequence version was designed to truncate the ZmZrp2 promoter so that 1.0 Kb of the 5' end of the original polynucleotide sequence was removed. In addition the *Zea mays* Ubiquitin 1 intron (SEQ ID NO: 2) was fused to the truncated polynucleotide sequence promoter to enhance gene expression strength. The ZmZrp2 promoter and *Zea mays* Ubiquitin 1 intron (ZmUbi1 intron) fusion is provided as SEQ ID NO:6.

Gene specific downstream polynucleotide sequences referred to as 3' untranslated regions (3' UTR) are commonly multifunctional in vivo. RNA processing and maturation have been recognized as key control points for postranscriptional control of eukaryotic gene expression (Szostak and Gebauer, 2012; Wilusz and Spector, 2010; Barrett et al., 2012; and Moore, 2005). These polynucleotide sequences can influence rate of nuclear export, subcellular localization, transcript stability and translation. In addition, 3' UTRs are key target sites for control by small non-coding RNAs. While many of these mechanisms down regulate gene expression, such regulation can also be used to effectively localize transcripts to specific cell types for stable accumulation and subsequent gene expression (Patel et al., 2006). From the assessment of the contiguous chromosomal sequence associated with the Zm Zrp2 promoter (SEQ ID NO:1) a 500 bp 3' UTR polynucleotide sequence (SEQ ID NO: 3) was identified and isolated for use in expression of heterologous coding sequences along with the truncated ZmZrp2 promoter fused to the ZmUbi1 intron (SEQ ID NO:2) to produce SEQ ID NO:6.

Example 2: Vector Construction (pDAB113281 and pDAB113231)

Figure 2:
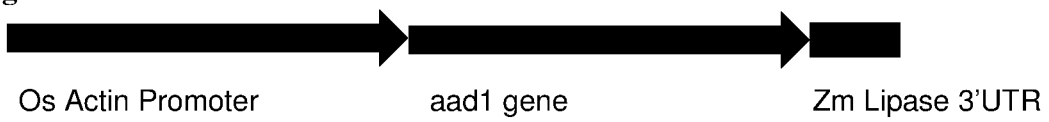
FIG. 2: This figure is a schematic of the selectable marker gene cassette on pDAB113281 and pDAB113231 which contains the *Oryza sativa* promoter (labeled as "OS Actin Promoter") that is operably linked to the aad-1 gene (labeled as "aad1 gene") and the *Zea mays* Lipase 3'-UTR (labeled as "Zm Lipase 3'UTR").

The pDAB113281 vector was built to incorporate the novel combination of regulatory polynucleotide sequences flanking a transgene. The vector construct pDAB113281 contained a gene expression cassette, in which the phi-yfp transgene (Phi-yellow fluorescent protein; Clontech, Mountain View, Calif.) was driven by the truncated promoter from the *Zea mays* Zrp2 gene of SEQ ID NO:1 (ZmZrp2), fused to an intron from the *Zea mays* Ubiquitin 1 gene of SEQ ID NO:2 (ZmUbi1 intron) and flanked by *Zea mays* Zrp2 3' UTR of SEQ ID NO:3. A diagram of this gene expression cassette is shown in FIG. 1 and is provided as SEQ ID NO:4. The vector also contained a selectable marker gene expression cassette that contained the aad-1 transgene (U.S. Pat. No. 7,838,733) driven by the *Oryza sativa* Actin promoter (U.S. Pat. No. 5,641,876) and was terminated by the *Zea mays* Lipase 3' UTR (U.S. Pat. No. 7,179,902). A diagram of this gene expression cassette is shown in FIG. 2 and is provided as SEQ ID NO:5. This construct was built by synthesizing the newly designed promoter from a *Zea mays* Zrp2 gene (ZmZrp2 promoter) and cloning the promoter into a Gateway™ (Life Technologies) entry vector using a third party provider (DNA2.0, Menlo Park, Calif.). The resulting entry vector contained the ZmZrp2 promoter driving the phi-yfp gene, and was integrated into a destination vector using the Gateway™ cloning system (Life Technologies) and electroporated into *Agrobacterium tumefaciens* strain LBA4404, resulting in the final superbinary (reviewed by Komori et al. (2006), *Methods in Molecular Biology* (K. Wang, ed.) No. 343; *Agrobacterium* Protocols, 2nd Edition, Vol. 1, Humana Press Inc., Totowa, NT, pp. 15-41; and Komori et al. (2007), *Plant Physiol.* 145:1155-60) construct pDAB113281. Clones of pDAB113281 were obtained and plasmid DNA was isolated and confirmed via restriction enzyme digestions and sequencing. The resulting construct contained a combination of regulatory elements that drive expression of a transgene preferentially in maize root tissues.

Figure 3:
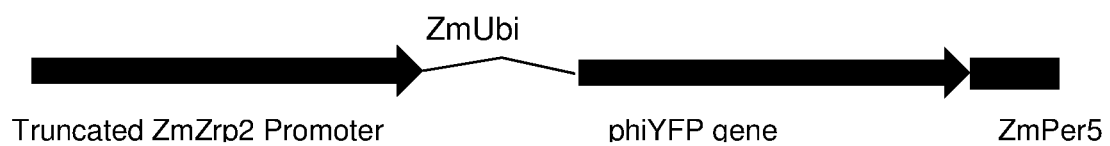
FIG. 3: This figure is a schematic of the gene of interest gene cassette on pDAB113231 which contains the *Zea mays* Zrp2 promoter of SEQ ID NO:1 (labeled as "Truncated ZmZrp2 Promoter") that is operably linked to the *Zea mays* Ubiquitin 1 intron of SEQ ID NO:2 (labeled as "ZmUbi1 Intron") and the *Zea mays* Per5 3'-UTR (labeled as "ZmZrp2 3'UTR"). These regulatory elements are operably linked to the phi-yfp gene (labeled as "phiYFP gene").

A second vector was built to incorporate the novel combination of promoter regulatory polynucleotide sequences flanking a transgene. The vector construct pDAB113231 contained a gene expression cassette, in which the phi-yfp transgene (Phi-yellow fluorescent protein; Clontech, Mountain View, Calif.) was driven by the truncated promoter from the *Zea mays* Zrp2 gene of SEQ ID NO:1 (ZmZrp2), fused to an intron from the *Zea mays* Ubiquitin 1 gene of SEQ ID NO:2 (ZmUbi1 intron) and flanked by *Zea mays* Per5 3' UTR (U.S. Pat. No. 6,699,984). A diagram of this gene expression cassette is shown in FIG. 3 and is provided as SEQ ID NO:9. The vector also contained a selectable marker gene expression cassette that contained the aad-1 transgene (U.S. Pat. No. 7,838,733) driven by the *Oryza sativa* Actin promoter (U.S. Pat. No. 5,641,876) and was terminated by the *Zea mays* Lipase 3' UTR (U.S. Pat. No. 7,179,902). A diagram of this gene expression cassette is shown in FIG. 2 and is provided as SEQ ID NO:5. This construct was built by synthesizing the newly designed promoter from a *Zea mays* Zrp2 gene (ZmZrp2 promoter) and cloning the promoter into a Gateway™ (Life Technologies) entry vector using a third party provider (DNA2.0, Menlo Park, Calif.). The resulting entry vector contained the ZmZrp2 promoter driving the phi-yfp gene, and was integrated into a destination vector using the Gateway™ cloning system (Life Technologies) and electroporated into *Agrobacterium tumefaciens* strain LBA4404, resulting in the final superbinary construct pDAB113231. Clones of pDAB113231 were obtained and plasmid DNA was isolated and confirmed via restriction enzyme digestions and sequencing. The resulting construct contained a combination of regulatory elements that drive expression of a transgene preferentially in maize root tissues.

Example 3: Maize Transformation

*Agrobacterium* Culture Initiation:

Glycerol stocks for pDAB113281 and pDAB113231 super binary constructs in the host *Agrobacterium tumefaciens* strain EHA105 were used to inoculate Luria Broth medium. Cultures were allowed to grow on a horizontal shaker set at 150 rpm at 26° C. for 16 hours. *Agrobacterium* cultures were diluted 1:5 in Luria Broth and grown for an additional 8 hours. Cultures were then pelleted by centrifuging at 3500 rpm for 15 minutes, suspended and diluted to an optical density (OD) of 0.2 in Induction media and placed on a shaker at 150 rpm for 16 hours. After induction, *Agrobacterium* cultures were pelleted and suspended in MS Inoculation medium ((2.2 g/L MS salts, 68.4 g/L sucrose, 36 g/L glucose, 115 mg/L L-proline, 2 mg/L glycine, 100 mg/L myo-Inositol, 0.05 mg/L nicotinic acid, 0.5 mg/L pyridoxine HCl, 0.5 mg/L thiamine, 200 µM acetosyringone) to a final OD of 0.25. Ears of *Zea mays* c.v. B104 containing immature embryos were grown in the greenhouse and were harvested at 12-15 days post pollination. The *Zea mays* c.v. B104 ears were grown with a 16:8 light/dark photoperiod with a daytime temp average of 27° C. and night temperature averages of 19° C. Supplemental light was provided as 50% High Pressure Sodium and 50% Metal Halide. The ears of corn were surface sterilized with 70% ethanol following a standard protocol.

Agrobacterium Mediated Transformation of Maize Immature Embryos:

Experimental constructs pDAB113281 and pDAB113231 were transformed into *Zea mays* via *Agrobacterium*-mediated transformation of immature embryos isolated from the inbred line, *Zea mays* c.v. B104. The method used is similar to those published by Ishida et al., (1996) Nature Biotechnol 14:745-750 and Frame et al., (2006) Plant Cell Rep 25: 1024-1034, but with several modifications and improvements. An example of a method used to produce transgenic events in maize is given in U.S. Patent App. Pub. No. US 2013/0157369 A1, beginning with the embryo infection and co-cultivation steps.

Putative $T_0$ transgenic plantlets were transplanted from Phytatrays™ (Sigma-Aldrich; St. Louis, Mo.) to a DI water saturated QPlug 60™ (International Horticultural Technologies), covered with humidomes (Arco Plastics Ltd.), and then hardened-off in a growth room (16-hour 225 μM light cycle at 26° C./8-hour dark cycle at 23° C. and RH at 100%) When plants reached the V3-V4 developmental stage (3-4 leaf collars visible), they were transplanted into Sunshine Custom Blend 160 soil mixture and grown to flowering in the greenhouse (Light Exposure Type: Photo or Assimilation; High Light Limit: 1200 PAR; 16-hour day length; 27° C. day/24° C. night). The plants were analyzed for transgene copy number by qPCR assays using primers designed to detect relative copy numbers of the transgenes, and putative single copy events selected for advancement were transplanted into 5 gallon pots.

Example 4: Molecular Confirmation of Copy Number at $T_0$

The status of the transgene insertion in $T_0$ plants was determined by Taqman™ Real-Time PCR. All isolated events were sampled to ascertain low-copy number (1-2 copies) of the aad-1 gene and to determine the status of the vector backbone by absence of the Spectinomycin resistance gene. Samples were taken from young leaf tissue at the V1 stage of development and DNA was isolated using the Qiagen Biosprint 96 Plant Kits®. The Roche Light Cycler480™ system was used to determine the transgene copy number. The method utilized a duplex TaqMan® reaction that employed oligonucleotides specific to the aad-1 gene and to the endogenous *Zea mays* reference gene, expansin 2 (Genbank Accession No: AF332170), in a single assay. Copy number and zygosity were determined by measuring the intensity of aad-1 specific fluorescence, relative to the invertase-specific fluorescence, as compared to known copy number standards.

Example 5: Molecular Confirmation of Hemizygote Lines at T1

Genotyping by Real-Time qPCR:

The zygosity of the transgene insertion in T1 plants was determined by Taqman™ Real-Time PCR of the aad-1 gene and normalized using the invertase IV gene (Genbank Accession No: U16123.1) as the internal control in a duplex reaction. Samples were taken from T1 young leaf tissue at V1 and DNA was isolated using the Qiagen Biosprint 96 Plant Kit®. DNA quality was confirmed by visualization on a 1.5% agarose gel. A Picogreen® assay (Invitrogen) was run to quantify the DNA. Assays for qPCR were run to determine the zygosity and copy number of all events grown in the greenhouse. Assays were run by triplicate on Roche LightCycler 48011 system that employed oligonucleotides specific to the aad-1 gene and to the endogenous *Zea mays* reference gene. The number of copies of the gene of interest was calculated using the comparative Ct method (ΔΔCt).

Example 6: Molecular Confirmation of Transcript Accumulation

Total RNA was isolated and purified from frozen root and noon-root tissue (leaf, immature male flower, pollen, silk, husk, embryo and endosperm) samples in a 96-well plate format using the MagMAX™ 96 Total RNA Isolation Kit (Life Technologies). Quantitative real-time PCR assays, were performed using specific oligonucleotides and probes (Roche Universal Probe Library) for the phi-yfp gene as well as for the reference genes used for each specific tissue. Raw data in the form of cycle threshold (Cq) for the target phi-yfp gene assay was normalized to the internal reference gene for each tissue. Target to reference ratios were calculated according to the formula $2^{-(CqTARGET-CqREF)}$. The geometric mean of two reference gene normalized ratios was calculated to increase accuracy (Vandesompele et al., 2002). Samples from each tissue used a specific combination of reference gene pairs optimized for that particular tissue. For statistical analysis, normalized transcript abundance data was transformed to natural logarithmic values to generate a normalized distribution for cross-comparisons. The normalized, log transformed target to reference ratios are referred to as log M T/R in all figures in this report and was generated using JMP® Pro 10.0.2 software.

Example 7: Molecular Confirmation of Protein Accumulation

PhiYFP protein abundance values were quantitated for all tissue types obtained from different stages of growth and development. Protein accumulation values obtained for pDAB113281 and pDAB113231 plants were compared to the same events used as reference for the transcript abundance data. The PhiYFP protein quantification values were then normalized to nanogram of PhiYFP per miligram (ng/mg) of total soluble protein and the values were converted to Log 2 scale for data analysis using JMP® Pro 10.0.2 software. Total soluble protein was isolated and quantified in 96 well format following standard methods. A total of 600 μL of extraction buffer separated in two 300 μL aliquots was used for all tissues and stages sampled. The mass spectrometer used for this method was an Applied Biosystems MDS Sciex 5500 Q TRAP™ hybrid triple quad, utilizing a Turbo V ESI™ source housing fitted with a TSI Probe™. All methods and data files were created using the software version Analyst 1.5.2™. The samples were introduced into the mass spectrometer via a Waters Acquity UPLC™ system. Reverse phase chromatography was performed at 400 μL/min using a Waters BEH130 C18™ 1.7 μm 2.1×50 mm column at a temperature of 50° C. Column loading conditions were 95% A(H$_2$O/0.1% formic acid)/5% B (acetonitrile/0.1% formic acid) with a gradient to 45% B in three minutes. The column was regenerated with a 0.5 minute hold at 90% B, and then re-equilibrated to 5% B for 0.5 minute. Sample injection volumes were 20 μL. Two PhiYFP tryptic peptide fragments were chosen as valid surrogates for PhiYFP protein in terms of peptide stability, signal sensitivity, signal reproducibility, matrix suppression, and isobar interference.

Example 8: Crop Transformation of Genes Operably Linked to the ZmZrp2 Regulatory Elements The ZmZrp2 regulatory elements, for example the 3' UTR element of SEQ ID NO:3 and the ZmZrp2 promoter (SEQ ID NO:1) and the ZmUbi1 intron (SEQ ID NO:2) combined elements of SEQ ID NO:6 as provided in pDAB113281, resulted in phi-yfp gene expression primarily in root tissues. The phi-yfp gene transcript abundance in leaf tissue of *Zea mays* transformed with pDAB113281 at both the V2 and V10 stages accumulated significantly lower as compared to root tissues. Although some transcript is detected for the ZmZrp2 constructs in leaf tissue, the levels of expression driven by the combined ZmZrp2 promoter element of SEQ ID NO:1 and the ZmUbi1 intron of SEQ ID NO:2, i.e., combined elements of SEQ ID NO:6, are lower than those observed in root tissues when compared as a percentage to the expression of the phi-yfp gene driven by the benchmark *Zea mays* Ubiquitin 1 promoter elements (Christensen A H, Sharrock R A, Quail P H (1992) Maize polyubiquitin gene: structure, thermal perturbation of expression and transcript splicing, and promoter activity following transfer to protoplasts by electroporation. Plant Mol Biol 18: 675-689). Table 1 summarizes root and leaf transcript abundance for the phi-yfp reporter gene in the plants transformed with pDAB113281 constructs containing the "ZmZrp2 v3 N" regulatory elements (i.e., 3' UTR of SEQ ID NO:3, and promoter elements of SEQ ID NO:1 and SEQ ID NO:2 combined as SEQ ID NO:6) as a percentage of transcript abundance for the phi-yfp reporter gene driven by the *Zea mays* Ubiquitin 1 promoter elements. Also provided is the root and leaf transcript abundance for the phi-yfp reporter gene in the plants containing pDAB113231 constructs transformed with the "ZmZrp2 v3" regulatory elements (i.e. 3' UTR of *Zea mays* Per 5 3' UTR (U.S. Pat. No. 6,699,984), and promoter elements of SEQ ID NO:1 and SEQ ID NO:2 combined as SEQ ID NO:6) as a percentage of transcript abundance for the phi-yfp reporter gene driven by the *Zea mays* Ubiquitin 1 promoter elements. It is noteworthy that the plants containing pDAB113281 constructs containing the "ZmZrp2 v3 N" regulatory elements (i.e., 3' UTR of SEQ ID NO:3, and promoter elements of SEQ ID NO:1 and SEQ ID NO:2 combined as SEQ ID NO:6) drove higher levels of expression in the V2 root branch tissues. As described previously the constructs containing the ZmZrp2 v3 promoter elements (e.g. pDAB113281 and pDAB113231) expressed the phi-yfp gene in leaf tissue, however, the expression levels were markably lower than those observed in root tissues when compared as a percentage of the benchmark ZmUbi1 promoter. Accordingly, the use of the isolated ZmZrp2 3' UTR improves the preferential expression of PhiYFP in root tissues.

TABLE 1

The mean phi-yfp reporter gene log transcript abundance in root and leaf tissues as a percentage of the transcript abundance expression of a reporter gene driven by the *Zea mays* Ubiquitin 1 promoter elements.

| RE Construct | V2 Root Tip | V2 Root Branch | V6 Root Tip | V2 Leaf | V10 Leaf |
|---|---|---|---|---|---|
| ZmZrp2 v3 (ZmPer5 3' UTR) are transgenic plants containing the pDAB113231 construct | 15.5 | 29.9 | 22.5 | 4.5 | 7.6 |
| ZmZrp2 v3 N (ZmZrp2 3' UTR) are transgenic plants containing the pDAB113281 construct | 14.7 | 49.7 | 18.9 | 3.8 | 11.3 |

It was of further interest to analyze transcript levels in male reproductive tissues because transcript accumulating in these tissues could potentially cause undesirable agronomic penalties in plants. It was observed that the lower transcript levels were present in immature male flowers (IMF) and pollen tissues when the truncated ZmZrp2 promoter (SEQ ID NO:1) was used in combination with the ZmZrp2 3' UTR (SEQ ID NO:3). These results are beneficial as such an expression pattern is primarily directed in preferred tissues at specific levels. A summary comparison of transcript levels in all reproductive tissues is displayed in Table 2. For this comparison, transcript levels for the expression of the ZmZrp2 promoter and phi-yfp reporter gene as terminated by the ZmPer5 3' UTR (ZmZrp2 v3) of pDAB113231 were compared to transcript levels for the expression of the ZmZrp2 promoter and phi-yfp reporter gene terminated by the ZmZrp2 3' UTR (ZmZrp2 v3 N) of pDAB113281. The results are shown as a percentage of transcript accumulation levels observed with the reference events transformed with *Zea mays* Ubiquitin 1 promoter elements and terminated by the ZmPer5 3' UTR. It was observed that the phi-yfp reporter gene was expressed at lower levels in the immature male flower (IMF), pollen, embryo and endosperm for the constructs containing the combination of the ZmZrp2 3' promoter and the ZmZrp2 3' UTR (i.e. pDAB113281). The resulting data supports that the ZmZrp2 3' UTR (SEQ ID NO:3) is best used in combination with the ZmZrp2 promoter (SEQ ID NO:1) to specifically drive expression of genes of interest that require similar patterns of expression in specific tissues (i.e., root tissues). The low levels of expression in non-root tissues and the preferential expression in root tip and branch tissues make this novel combination of regulatory elements unique and useful providing additional variability when designing multigenic constructs and improving the probability of success.

TABLE 2

The mean phi-yfp reporter gene log transcript abundance in reproductive tissues as a percentage of the transcript abundance expression of a reporter gene driven by the *Zea mays* Ubiquitin 1 promoter elements.

| RE Construct | IMF | Pollen | Silk | Husk | Embryo | Endosperm |
|---|---|---|---|---|---|---|
| ZmZrp2 v3 (ZmPer5 3' UTR) are transgenic plants containing the pDAB113231 construct | 20.9 | 15.8 | 17.7 | 17.7 | 22.6 | 2.5 |
| ZmZrp2 v3 N (ZmZrp2 3' UTR) are transgenic plants containing the pDAB113281 construct | 9.6 | 4.6 | 21.3 | 28.8 | 16.2 | 2.5 |

It was further observed that PhiYFP protein accumulated in root tissues of *Zea mays* at V2 and V6 in the transgenic plants transformed with pDAB113281. These data are in agreement with the observations for transcript accumulation (provided above) and further support the use of the ZmZrp2 3' UTR (SEQ ID NO:3) when building constructs with the gene of interest under the control of the ZmZrp2 promoter (SEQ ID NO:1). For the leaf, immature male flower, silk, husk, embryo and endosperm tissues that were assayed the values obtained for PhiYFP protein accumulation, were reported as zero (i.e. "0") or below the limit of quantification of the LC/MS/MS method protocol described above. However, PhiYFP protein was detected in pollen tissues, but at lower levels than the PhiYFP protein expression in root tissues (Table 3). Accordingly, the use of the ZmZrp2 regulatory elements, including the isolated ZmZrp2 3' UTR of SEQ ID NO:3) improves the preferential expression of PhiYFP in root tissues.

TABLE 3

PhiYFP protein abundance in root and pollen tissues.

| Tissue | Protein Accumulation Mean Log2 ng/mL |
|---|---|
| Root V2 | 1.6 |
| Root V6 | 1.4 |
| Pollen | 1.0 |

Example 9: *Agrobacterium*-Mediated Transformation of Genes Operably Linked to the *Zea mays* Zrp2 Promoter Fused to the *Zea mays* Ubiquitin 1 Intron or to Genes Operably Linked to the *Zea mays* Zrp2 3' UTR Soybean may be transformed with genes operably linked to the *Zea mays* Zrp2 promoter fused to the *Zea mays* Ubiquitin 1 intron or to genes operably linked to the *Zea mays* Zrp2 3' UTR by utilizing the same techniques previously described in Example #11 or Example #13 of patent application WO 2007/053482.

Cotton may be transformed with genes operably linked to the *Zea mays* Zrp2 promoter fused to the *Zea mays* Ubiquitin 1 intron or to genes operably linked to the *Zea mays* Zrp2 3' UTR by utilizing the same techniques previously described in Examples #14 of U.S. Pat. No. 7,838,733 or Example #12 of patent application WO 2007/053482 (Wright et al.).

Canola may be transformed with genes operably linked to the *Zea mays* Zrp2 promoter fused to the *Zea mays* Ubiquitin 1 intron or to genes operably linked to the *Zea mays* Zrp2 3' UTR by utilizing the same techniques previously described in Example #26 of U.S. Pat. No. 7,838,733 or Example #22 of patent application WO 2007/053482 (Wright et al.).

Wheat may be transformed with genes operably linked to the *Zea mays* Zrp2 promoter fused to the *Zea mays* Ubiquitin 1 intron or to genes operably linked to the *Zea mays* Zrp2 3' UTR by utilizing the same techniques previously described in Example #23 of patent application WO 2013/116700A1 (Lira et al.).

Rice may be transformed with genes operably linked to the *Zea mays* Zrp2 promoter fused to the *Zea mays* Ubiquitin 1 intron or to genes operably linked to the *Zea mays* Zrp2 3' UTR by utilizing the same techniques previously described in Example #19 of patent application WO 2013/116700A1 (Lira et al.).

Example 10: *Agrobacterium*-Mediated Transformation of Genes Operably Linked to the Zm Zrp2 Regulatory Elements In light of the subject disclosure, additional crops can be transformed according to embodiments of the subject disclosure using techniques that are known in the art. For *Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," Transgenic Res. 2003 October; 12(5): 587-96.). For *Agrobacterium*-mediated transformation of sorghum, see, e.g., Zhao et al., "*Agrobacterium*-mediated sorghum transformation," Plant Mol Biol. 2000 December; 44(6):789-98. For *Agrobacterium*-mediated transformation of barley, see, e.g., Tingay et al., "*Agrobacterium tumefaciens*-mediated barley transformation," The Plant Journal, (1997) 11: 1369-1376. For *Agrobacterium*-mediated transformation of wheat, see, e.g., Cheng et al., "Genetic Transformation of Wheat Mediated by *Agrobacterium tumefaciens*," Plant Physiol. 1997 November; 115(3):971-980. For *Agrobacterium*-mediated transformation of rice, see, e.g., Hiei et al., "Transformation of rice mediated by *Agrobacterium tumefaciens*," Plant Mol. Biol. 1997 September; 35(1-2):205-18.

The Latin names for these and other plants are given below. It should be clear that other (non-*Agrobacterium*) transformation techniques can be used to transform genes operably linked to the promoter or a 3' UTR of Zm Zrp2, for example, into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa*, *Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense*, and *frutescens*), Lettuce (*Lactuca sativa, perennis*, and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (*Pisum, Vigna*, and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynodon*, and other genera), Clover (*Trifolium*), Vetch (*Vicia*). Transformation of such plants, with genes operably linked to the promoter or a 3' UTR of Zm Zrp2, for example, is contemplated in embodiments of the subject disclosure.

Use of the promoter or a 3' UTR of Zm Zrp2 to drive operably linked genes can be deployed in many deciduous and evergreen timber species. Such applications are also within the scope of embodiments of this disclosure. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp.), and pine (*Pinus* spp.).

Use of the promoter or a 3' UTR of Zm Zrp2 to drive operably linked genes can be deployed in ornamental and fruit-bearing species. Such applications are also within the scope of embodiments of this disclosure. Examples include, but are not limited to; rose (*Rosa* spp.), burning bush (*Euonymus* spp.), petunia (*Petunia* spp.), begonia (*Begonia* spp.), rhododendron (*Rhododendron* spp.), crabapple or apple (*Malus* spp.), pear (*Pyrus* spp.), peach (*Prunus* spp.), and marigolds (*Tagetes* spp.).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A nucleic acid vector comprising a 3' UTR operably linked to:
   a) a heterologous polylinker sequence; or
   b) a non-*Zea mays* Zrp2 polynucleotide sequence,
   wherein said 3' UTR comprises a polynucleotide sequence that has at least 97% sequence identity with SEQ ID NO:3.

2. The nucleic acid vector of claim 1, wherein said 3' UTR is 500 bp in length.

3. The nucleic acid vector of claim 1, wherein said 3' UTR consists of a polynucleotide sequence that has at least 97% sequence identity with SEQ ID NO:3.

4. The nucleic acid vector of claim 1, further comprising a sequence encoding a selectable maker.

5. The nucleic acid vector of claim 1, wherein said non-*Zea mays* Zrp2 polynucleotide sequence is a transgene.

6. The nucleic acid vector of claim 5, wherein the transgene encodes a selectable marker or a gene product conferring insecticidal resistance, herbicide tolerance, expression of an RNAi, nitrogen use efficiency, water use efficiency, or nutritional quality.

7. The nucleic acid vector of claim 1, further comprising a promoter polynucleotide sequence of SEQ ID NO:1, or a promoter polynucleotide sequence of SEQ ID NO:6, wherein the promoter sequence is operably linked to said polylinker or said non-*Zea mays* Zrp2 polynucleotide sequence.

8. The nucleic acid vector of claim 1, further comprising an intron sequence.

9. The nucleic acid vector of claim 7, wherein said promoter has below ground tissue specific expression.

* * * * *